(12) United States Patent
Im et al.

(10) Patent No.: US 12,187,823 B2
(45) Date of Patent: Jan. 7, 2025

(54) LIGAND COMPOUND, TRANSITION METAL COMPOUND, AND CATALYST COMPOSITION INCLUDING THE SAME

(71) Applicant: LG Chem, Ltd., Seoul (KR)

(72) Inventors: Seul Ki Im, Daejeon (KR); Eun Ji Shin, Daejeon (KR); Seok Pil Sa, Daejeon (KR); Ki Soo Lee, Daejeon (KR); Bun Yeoul Lee, Daejeon (KR); Jun Won Baek, Daejeon (KR); Hyun Ju Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 725 days.

(21) Appl. No.: 17/419,886

(22) PCT Filed: Apr. 24, 2020

(86) PCT No.: PCT/KR2020/005437
§ 371 (c)(1),
(2) Date: Jun. 30, 2021

(87) PCT Pub. No.: WO2020/218874
PCT Pub. Date: Oct. 29, 2020

(65) Prior Publication Data
US 2022/0049031 A1 Feb. 17, 2022

(30) Foreign Application Priority Data
Apr. 26, 2019 (KR) .................. 10-2019-0049172

(51) Int. Cl.
*C08F 210/06* (2006.01)
*C07F 7/08* (2006.01)

(52) U.S. Cl.
CPC .......... *C08F 210/06* (2013.01); *C07F 7/0814* (2013.01)

(58) Field of Classification Search
None
See application file for complete search history.

(56) References Cited

U.S. PATENT DOCUMENTS

2002/0137845 A1  9/2002  Boussie et al.
2002/0142912 A1  10/2002 Boussie et al.
(Continued)

FOREIGN PATENT DOCUMENTS

CN    105849116 A    8/2016
CN    106317385 A    1/2017
(Continued)

OTHER PUBLICATIONS

Kundu. A. et al., "Direct ortho-C?H Aminoalkylation of 2?Substituted Pyridine Derivatives Catalyzed by Yttrium Complexes with N,N ?—Diarylethylenediamido Ligands" Journal Of The American Chemical Society, May 2018, pp. 7332-7342, vol. 140.
(Continued)

*Primary Examiner* — Catherine S Branch
(74) *Attorney, Agent, or Firm* — Lerner David LLP

(57) ABSTRACT

A ligand compound having a novel structure, a transition metal compound including the same, a catalyst composition including the transition metal compound, and a method of preparing an olefin polymer using the catalyst composition are disclosed herein. In some embodiments, the transition metal compound is represented by Formula 1. In some embodiments, the ligand compound is represented by Formula 2.

10 Claims, 14 Drawing Sheets

(56) References Cited

U.S. PATENT DOCUMENTS

| | | |
|---|---|---|
| 2002/0147288 A1 | 10/2002 | Boussie et al. |
| 2002/0156279 A1 | 10/2002 | Boussie et al. |
| 2002/0173419 A1 | 11/2002 | Boussie et al. |
| 2002/0177711 A1 | 11/2002 | LaPointe et al. |
| 2003/0176611 A1 | 9/2003 | Stevens et al. |
| 2003/0194575 A1 | 10/2003 | Tau et al. |
| 2003/0195299 A1 | 10/2003 | Stevens et al. |
| 2003/0195300 A1 | 10/2003 | Stevens et al. |
| 2003/0204017 A1 | 10/2003 | Stevens et al. |
| 2004/0082750 A1 | 4/2004 | Tau et al. |
| 2004/0087751 A1 | 5/2004 | Tau et al. |
| 2004/0122247 A1 | 6/2004 | Boussie et al. |
| 2004/0209765 A1 | 10/2004 | Boussie et al. |
| 2004/0220050 A1 | 11/2004 | Frazier et al. |
| 2004/0220051 A1 | 11/2004 | Coalter, III et al. |
| 2004/0242784 A1 | 12/2004 | Tau et al. |
| 2004/0249084 A1 | 12/2004 | Stevens et al. |
| 2005/0043470 A1 | 2/2005 | Stevens et al. |
| 2005/0054800 A1 | 3/2005 | Tau et al. |
| 2005/0113524 A1 | 5/2005 | Stevens et al. |
| 2005/0209472 A1 | 9/2005 | Vogel |
| 2005/0245686 A1 | 11/2005 | Stevens et al. |
| 2006/0004167 A1 | 1/2006 | Tau et al. |
| 2006/0135722 A1 | 6/2006 | Boussie et al. |
| 2006/0142494 A1 | 6/2006 | Stevens et al. |
| 2006/0142497 A1 | 6/2006 | Stevens et al. |
| 2006/0241255 A1 | 10/2006 | Coalter et al. |
| 2006/0247483 A1 | 11/2006 | McConville et al. |
| 2007/0122613 A1 | 5/2007 | Stevens et al. |
| 2007/0249798 A1 | 10/2007 | Stevens et al. |
| 2008/0269419 A1 | 10/2008 | Hustad |
| 2008/0293899 A1 | 11/2008 | McConville et al. |
| 2015/0152301 A1 | 6/2015 | Brandstadt et al. |
| 2017/0081350 A1 | 3/2017 | Facchetti et al. |
| 2018/0134827 A1 | 5/2018 | Hagadorn et al. |
| 2018/0170954 A1 | 6/2018 | Facchetti et al. |
| 2018/0194872 A1 | 7/2018 | Holtcamp et al. |
| 2018/0201698 A1 | 7/2018 | Hagadorn et al. |
| 2018/0201700 A1 | 7/2018 | Holtcamp et al. |
| 2018/0244817 A1 | 8/2018 | Hagadorn et al. |
| 2019/0233452 A1 | 8/2019 | Facchetti et al. |

FOREIGN PATENT DOCUMENTS

| | | |
|---|---|---|
| JP | 2001048925 A | 2/2001 |
| JP | 2008533047 A | 8/2008 |
| JP | 2014520949 A | 8/2014 |
| JP | 2017504569 A | 2/2017 |
| KR | 20070117675 A | 12/2007 |
| KR | 20150082908 A | 7/2015 |
| KR | 20180025319 A | 3/2018 |
| KR | 20180055531 A | 5/2018 |
| WO | 0238628 A2 | 5/2002 |
| WO | 03040201 A1 | 5/2003 |
| WO | 2004024739 A1 | 3/2004 |
| WO | 2006096881 A1 | 9/2006 |
| WO | 2013012897 A1 | 1/2013 |

OTHER PUBLICATIONS

Baratta. W. et al., "Highly Productive CNN Pincer Ruthenium Catalysts for the Asymmetric Reduction of Alkyl Aryl Ketones" Chemistry A European Journal, Jan. 2009, pp. 726-732, vol. 15, Issue 3.

Jenishi. J. et al., "Synthesis of Chiral Nonracemic 1-(2-Pyridinyl) ethylamines: Stereospecific Introduction of Amino Function onto the 2-Pyridinylmethyl Carbon Center" The Journal of Organic Chemistry, Sep. 2004, pp. 6781-6789, vol. 69.

Song. D. et al., "Cyclometalated Tridentate C—N—N Ligands with an Amine or Amido Donor in Platinum(II) and Palladium(II) Complexes and a Novel Potassium Alkoxide Aggregate" Organometallics, Aug. 2004, pp. 4406-4413, vol. 23.

Extended European Search Report and European Search Opinion for European Patent Application No. 20795353.0 dated Feb. 8, 2022, 11 pages.

Kwon, S et al., "Preparation of Pincer Hafnium Complexes for Olefin Polymerization", "Molecules", Apr. 2019, p. 1676, vol. 24, No. 9, XP055880841.

Nagae, H et al., "Aminomethylation Reaction of ortho-Pyridyl C—H Bonds Catalyzed by Group 3 Metal Triamido Complexes", "Journal of the American Chemical Society", Jan. 2015, pp. 640-643, vol. 137, No. 2, XP055880844.

Wang, T et al., "Synthesis, structure and catalytic properties of CNN pincer palladium(ii) and ruthenium(ii) complexes with Nsubstituted-2-aminomethyl-6-phenylpyridines", "Dalton Transations", Jan. 2011, p. 8964-8976, vol. 40, No. 35, XP055880842.

Claudio De Rosa et al., "Expanding the Origin of Stereocontrol in Propene Polymerization Catalysis", American Chemical Society, published May 2016, pp. 3767-3770, vol. 6, No. 6, ACS Publications, Washington, D.C.

International Search Report for Application No. PCT/KR2020/005437, mailing dated Aug. 3, 2020, 5 pages.

Naser Rahimi et al., "Double and Reversible Alkyl Transfer from ZrBn4/HfBn4 to a Diiminepyridine Ligand", European Journal of Inorganic Chemistry, published Feb. 2019, pp. 1-8, No. 6, Wiley-VCH Verlag Gmbh & Co., Germany.

Xiaoyan Wang et al., "Syntheses of Well-Defined Functional Isotactic Polypropylenes via Efficient Copolymerization of Propylene with w-Halo-a-alkenes by Post-metallocene Hafnium Catalyst", Macromolecules, published Jan. 2014, pp. 552-559, vol. 47, No. 2.

Zheng Wang et al., "Carbocyclic-fused N,N,N-pincer ligands as ring-strain adjustable supports for iron and cobalt catalysts in ethylene oligo-/polymerization", Coordination Chemistry Reviews, available online Mar. 2018, pp. 92-108, vol. 363, Science Direct, Elsevier.

LIGAND COMPOUND, TRANSITION METAL COMPOUND, AND CATALYST COMPOSITION INCLUDING THE SAME

CROSS-REFERENCE TO RELATED APPLICATIONS

The present application is a national phase entry under 35 U.S.C. § 371 of International Application No. PCT/KR2020/005437, filed on Apr. 24, 2020, which claims priority from Korean Patent Application No. 10-2019-0049172, filed on Apr. 26, 2019, the entire contents of which are incorporated by reference herein.

TECHNICAL FIELD

The present invention relates to a ligand compound having a novel structure, a transition metal compound, and a catalyst composition including the same.

BACKGROUND ART

Transition metal pincer complexes have been widely applied in an organometallic catalyst field. Tridentate chelating pincer ligands are combined with a metal to form a planar structure with the metal at the center. Ligand-metal interaction is rigid and inflexible, and thus, high stability is provided.

For uniform olefin polymerization, an initial Zr-based metallocene catalyst has been led to a Ti-based half-metallocene, and finally to a post-metallocene having a bicyclopentadienyl ligand. Among the post-metallocenes developed, a pincer-type [$C^{naphthyl}$, $N^{pyridine}$, $N^{amido}$]HfMe$_2$ complex is a main catalyst. This complex has been developed in the early 2000s through high-throughput screening and extensively researched, and is applied in commercial processes.

Such a complex may introduce a large amount of alpha-olefin in an ethylene/alpha-olefin copolymerization, and may control the tacticity of propylene polymerization for preparing isotactic polypropylene. In addition, the benefit is the complete prevention of a β-elimination process which is unique chain transfer reaction which is inevitably generated during olefin polymerization performed using the conventional Zr-based metallocene and Ti-based half-metallocene catalysts.

Due to such characteristics, a polyolefin chain may be grown from an Hf-site, and a PO chain may be uniformly grown by adding an excessive amount of diethylzinc (Et2Zn) as a chain transfer agent on purpose, and the latter is referred to as coordinative chain transfer polymerization (CCTP). CCTP technique may be utilized well for the commercial production of an olefin block copolymer.

In addition, a polyolefin-polystyrene block copolymer may be synthesized through the anionic polymerization of styrene using a complex in a reaction after CCTP. As described above, a transition metal compound including a hafnium metal may be useful as a catalyst for producing olefin, and a great deal of research for improving catalyst performance by modifying thereof is being conducted.

PRIOR ART DOCUMENT

[Patent Document]
 Korean Laid-open Patent No. 10-2018-0055531

DISCLOSURE OF THE INVENTION

Technical Problem

An object of the present invention is to provide a ligand compound having a novel structure, a transition metal compound and a catalyst composition including the same.

Technical Solution

In order to solve the above-described tasks, the present invention provides a transition metal compound represented by the following Formula 1:

[Formula 1]

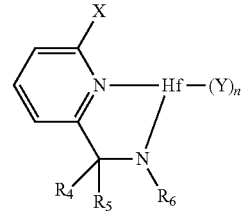

in Formula 1,
X is —Si($R_1$)($R_2$)($R_3$); or an aryl group of 6 to 20 carbon atoms, where any one among $R_1$ to $R_3$ or the aryl group of 6 to 20 carbon atoms may be combined with Hf to form a five-member ring,
$R_1$ to $R_3$ are each independently an alkyl group of 1 to 20 carbon atoms; a cycloalkyl group of 3 to 20 carbon atoms; an aryl group of 6 to 20 carbon atoms; an alkylaryl group of 7 to 20 carbon atoms; or an arylalkyl group of 7 to 20 carbon atoms,
$R_4$ and $R_5$ are each independently hydrogen; an alkyl group of 1 to 20 carbon atoms; an alkenyl group of 2 to 20 carbon atoms; an alkynyl group of 2 to 20 carbon atoms; a cycloalkyl group of 3 to 20 carbon atoms; an aryl group of 6 to 20 carbon atoms; an alkylaryl group of 7 to 20 carbon atoms; or an arylalkyl group of 7 to 20 carbon atoms,
$R_6$ is hydrogen; an alkyl group of 1 to 20 carbon atoms; a cycloalkyl group of 3 to 20 carbon atoms; an aryl group of 6 to 20 carbon atoms; an alkylaryl group of 7 to 20 carbon atoms; or an arylalkyl group of 7 to 20 carbon atoms, where if X is the aryl group of 6 to 20 carbon atoms, $R_6$ is not the aryl group of 6 to 20 carbon atoms or the alkylaryl group of 7 to 20 carbon atoms,
each Y is independently halogen; an alkyl group of 1 to 20 carbon atoms; an alkenyl group of 2 to 20 carbon atoms; an alkynyl group of 2 to 20 carbon atoms; a cycloalkyl group of 3 to 20 carbon atoms; an aryl group of 6 to 20 carbon atoms; an alkylaryl group of 7 to 20 carbon atoms; an arylalkyl group of 7 to 20 carbon atoms; a heteroaryl group of 5 to 20 carbon atoms; an alkoxy group of 1 to 20 carbon atoms; a substituted or unsubstituted aryloxy group of 5 to 20 carbon atoms; an alkylamino group of 1 to 20 carbon atoms; an arylamino group of 5 to 20 carbon atoms; an alkylthio group of 1 to 20 carbon atoms; an arylthio group of 5 to 20 carbon atoms; an alkylsilyl group of 1 to 20 carbon atoms; an arylsilyl group of 5 to 20 carbon atoms; a hydroxyl group; an amino group; a thio group; a silyl group; a cyano group; or a nitro group, and
n is an integer of 2 to 4.

Advantageous Effects

The novel transition metal compound of the present invention may be useful as a catalyst for polymerization reaction for preparing an olefin polymer having a high molecular weight.

BRIEF DESCRIPTION OF DRAWINGS

FIG. 1A shows a $^1$H NMR spectrum of the ligand compound of 2-1a.

FIG. 1B shows a $^{13}$C NMR spectrum of the ligand compound of 2-1a.

FIG. 2A shows a $^1$H NMR spectrum of the transition metal compound of 1-1a.

FIG. 2B shows a $^{13}$C NMR spectrum of the transition metal compound of 1-1a.

FIG. 5A shows a $^1$H NMR spectrum of the ligand compound of 2-2a.

FIG. 5B shows a $^{13}$C NMR spectrum of the ligand compound of 2-2a.

FIG. 6A shows a $^1$H NMR spectrum of the transition metal compound of 1-2a.

FIG. 6B shows a $^{13}$C NMR spectrum of the transition metal compound of 1-2a.

FIG. 7A shows a $^1$H NMR spectrum of the ligand compound of 2-3a.

FIG. 7B shows a $^1$H NMR spectrum and a $^{13}$C NMR spectrum of the ligand compound of 2-3a.

FIG. 8A shows a $^1$H NMR spectrum of the transition metal compound of 1-3a.

FIG. 8B shows a $^{13}$C NMR spectrum of the transition metal compound of 1-3a.

BEST MODE FOR CARRYING OUT THE INVENTION

Figure 1A:
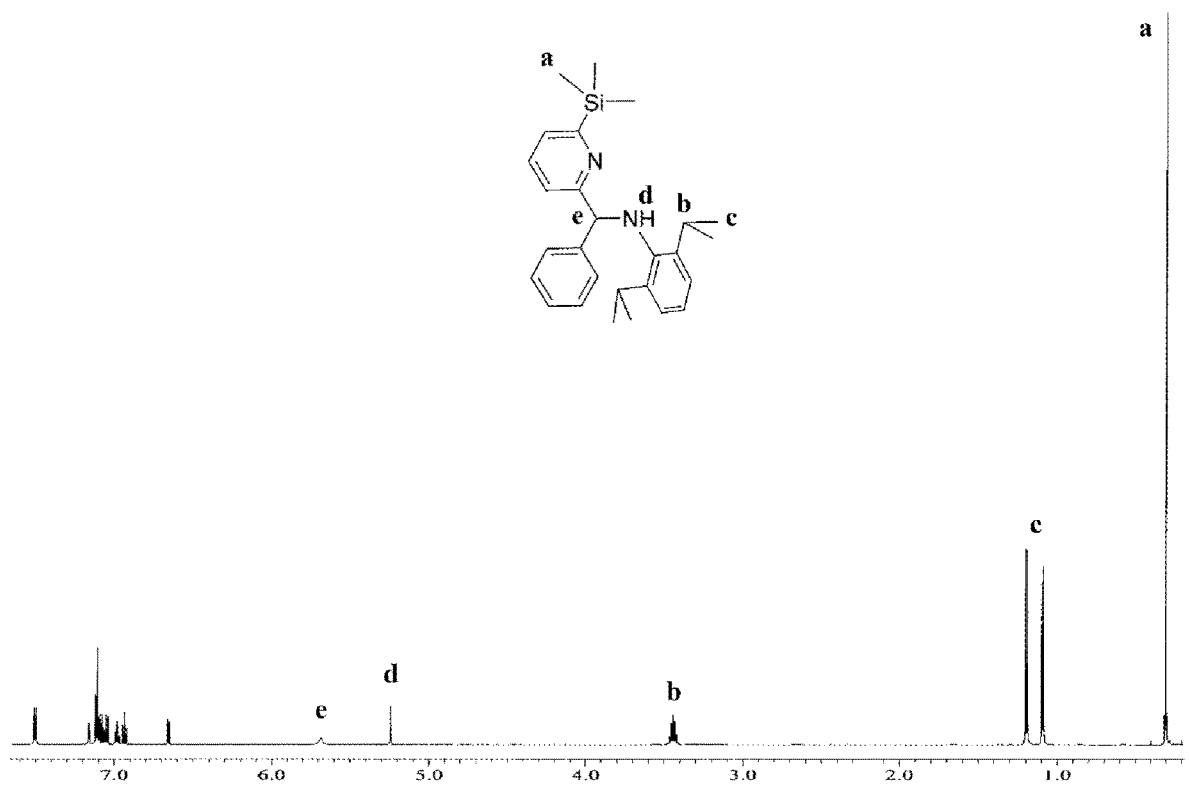

Hereinafter, the present invention will be explained in more detail to assist the understanding of the present invention.

It will be understood that words or terms used in the description and claims shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

The present invention provides a transition metal compound represented by the following Formula 1:

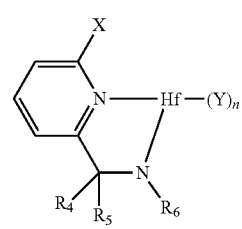

[Formula 1]

in Formula 1,

X is —Si(RO(R$_2$)(R$_3$); or an aryl group of 6 to 20 carbon atoms, where any one among R$_1$ to R$_3$ or the aryl group of 6 to 20 carbon atoms may be combined with Hf to form a five-member ring, R$_1$ to R$_3$ are each independently an alkyl group of 1 to 20 carbon atoms; a cycloalkyl group of 3 to 20 carbon atoms; an aryl group of 6 to 20 carbon atoms; an alkylaryl group of 7 to 20 carbon atoms; or an arylalkyl group of 7 to 20 carbon atoms, R$_4$ and R$_5$ are each independently hydrogen; an alkyl group of 1 to 20 carbon atoms; an alkenyl group of 2 to 20 carbon atoms; an alkynyl group of 2 to 20 carbon atoms; a cycloalkyl group of 3 to 20 carbon atoms; an aryl group of 6 to 20 carbon atoms; an alkylaryl group of 7 to 20 carbon atoms; or an arylalkyl group of 7 to 20 carbon atoms, R$_6$ is hydrogen; an alkyl group of 1 to 20 carbon atoms; a cycloalkyl group of 3 to 20 carbon atoms; an aryl group of 6 to 20 carbon atoms; an alkylaryl group of 7 to 20 carbon atoms; or an arylalkyl group of 7 to 20 carbon atoms, where if X is the aryl group of 6 to 20 carbon atoms, R$_6$ is not the aryl group of 6 to 20 carbon atoms or the alkylaryl group of 7 to 20 carbon atoms, each Y is independently halogen; an alkyl group of 1 to 20 carbon atoms; an alkenyl group of 2 to 20 carbon atoms; an alkynyl group of 2 to 20 carbon atoms; a cycloalkyl group of 3 to 20 carbon atoms; an aryl group of 6 to 20 carbon atoms; an alkylaryl group of 7 to 20 carbon atoms; an arylalkyl group of 7 to 20 carbon atoms; a heteroaryl group of 5 to 20 carbon atoms; an alkoxy group of 1 to 20 carbon atoms; a substituted or unsubstituted aryloxy group of 5 to 20 carbon atoms; an alkylamino group of 1 to 20 carbon atoms; an arylamino group of 5 to 20 carbon atoms; an alkylthio group of 1 to 20 carbon atoms; an arylthio group of 5 to 20 carbon atoms; an alkylsilyl group of 1 to 20 carbon atoms; an arylsilyl group of 5 to 20 carbon atoms; a hydroxyl group; an amino group; a thio group; a silyl group; a cyano group; or a nitro group, and n is an integer of 2 to 4.

If polymerization reaction is performed in the presence of an excessive amount of a chain transfer agent (for example, diethylzinc; $(Et)_2Zn$) with respect to a catalyst, an olefin polymer chain may undergo rapid transalkylation between zinc (Zn) and hafnium (Hf) for uniform propagation from dialkylzinc to accomplish living polymerization, and this is referred to as coordinative chain transfer polymerization (CCTP). The conventionally used metallocene catalysts precluded living polymerization due to a β-elimination process, and a small number of catalysts well-known as being applicable to CCTP enabled only homopolymerization of ethylene but made the copolymerization of ethylene and alpha-olefin through CCTP very difficult. Accordingly, the living polymerization through CCTP using a common transition metal compound as a catalyst to prepare a block copolymer was difficult.

On the contrary, the compound of the present invention is a pincer-type $[C^{silylmethyl}, N^{pyridine}, N^{amido}]HfMe_2$ or $[C^{naphthyl}, N^{pyridine}, N^{alkylamido}]HfMe_2$ complex and shows excellent alpha-olefin mixing capacity in the polymerization reaction of ethylene and alpha-olefin. Particularly, the molecular weight of an olefin polymer and the amount of the alpha-olefin change according to the amount of a chain transfer agent, and this shows that the compound of the present invention is successfully used in CCTP, and a β-elimination process hardly occurs to a negligible level. That is, the copolymerization of ethylene and alpha-olefin monomers may be performed by living polymerization through CCTP by using the hafnium compound of the present invention, and a block copolymer having diverse block components may be successfully prepared.

In addition, by converting the CCTP using the hafnium compound of the present invention to anionic styrene polymerization reaction, the synthesis of a polyolefin-polystyrene block copolymer may be possibly carried out. Like this, the hafnium compound of the present invention may be useful as a catalyst for preparing an olefin polymer, and this is unique characteristic which may be accomplished by the novel structure of the catalyst newly developed in the present invention.

Particularly, the catalyst of the present invention is a two-coordinate, or three-coordinate type novel catalyst and has a different structure from the conventional catalysts, and by using hafnium (Hf) other than zirconium (Zr), or titanium (Ti) as a transition metal, excellent catalyst activity and alpha-olefin mixing capacity may be achieved.

Particularly, to show excellent activity as an olefin polymerization catalyst, the chain transfer of a catalyst, a monomer, alkyl aluminum, etc., is required to decrease during polymerization reaction. The catalyst of the present invention is a branch type or bulky and introduces a substituent having large steric hindrance to prevent the chain transfer and improve the mixing capacity of alpha-olefin during performing polymerization reaction.

In Formula 1, $R_1$ to $R_3$ may be each independently an alkyl group of 1 to 20 carbon atoms; or an aryl group of 6 to carbon atoms, $R_4$ and $R_5$ may be each independently hydrogen; an alkyl group of 1 to 20 carbon atoms; or an aryl group of 6 to 20 carbon atoms, $R_6$ may be an alkyl group of 1 to 20 carbon atoms; a cycloalkyl group of 3 to 20 carbon atoms; or an aryl group of 6 to 20 carbon atoms, where $R_6$ may be substituted with an alkyl group of 1 to 20 carbon atoms, each Y may be independently an alkyl group of 1 to 20 carbon atoms; a substituted or unsubstituted cycloalkyl group of 3 to 20 carbon atoms; or a substituted or unsubstituted aryl group of 6 to 20 carbon atoms, and n may be 2 or 3.

In addition, particularly, in Formula 1, $R_1$ to $R_3$ may be each independently an alkyl group of 1 to 6 carbon atoms, or an aryl group of 6 to 12 carbon atoms, $R_4$ and $R_5$ may be each independently hydrogen; or an aryl group of 6 to 12 carbon atoms, $R_6$ may be an alkyl group of 1 to 12 carbon atoms; a cycloalkyl group of 6 to 12 carbon atoms; or an aryl group of 6 to 12 carbon atoms, where $R_6$ may be substituted with an alkyl group of 1 to 6 carbon atoms, each Y may be independently an alkyl group of 1 to 20 carbon atoms, and n may be 2 or 3.

According to an embodiment of the present invention, in Formula 1, X may be $-Si(R_1)(R_2)(R_3)$, where $R_1$ to $R_3$ may be each independently an alkyl group of 1 to 12 carbon atoms, an alkyl group of 1 to 6 carbon atoms, for example, an isopropyl group, $R_4$ may be hydrogen, $R_5$ may be an aryl group of 6 to 12 carbon atoms, for example, a phenyl group, $R_6$ may be an aryl group of 6 to 12 carbon atoms, which is substituted with an alkyl group of 1 to 6 carbon atoms, for example, a phenyl group which is substituted with an isopropyl group, and a substituent may be one or more.

According to an embodiment of the present invention, in Formula 1, X may be $-Si(R_1)(R_2)(R_3)$, where $R_1$ to $R_3$ may be each independently an alkyl group of 1 to 12 carbon atoms or an aryl group of 6 to 12 carbon atoms, where one or more among $R_1$ to $R_3$ may be alkyl groups of 1 to 12 carbon atoms and carbon adjacent to Si may be combined with Hf to form a five-member ring, $R_4$ may be hydrogen, $R_5$ may be an aryl group of 6 to 12 carbon atoms, for example, a phenyl group, $R_6$ may be an aryl group of 6 to 12 carbon atoms, which is substituted with an alkyl group of 1 to 6 carbon atoms, for example, a phenyl group which is substituted with an isopropyl group, and a substituent may be one or more.

According to an embodiment of the present invention, in Formula 1, X may be an aryl group of 6 to 20 carbon atoms, for example, a naphthyl group and at the same time, may be combined with Hf to form a five-member ring, $R_4$ may be hydrogen, $R_5$ may be an aryl group of 6 to 12 carbon atoms, for example, a phenyl group, and $R_6$ may be hydrogen; an alkyl group of 1 to 20 carbon atoms; a cycloalkyl group of 3 to 20 carbon atoms; or an alkylaryl group of 7 to 20 carbon atoms, and in an embodiment where X is the aryl group of 6 to 20 carbon atoms, $R_6$ is not the aryl group of 6 to 20 carbon atoms or the alkylaryl group of 7 to 20 carbon atoms.

Particularly, the transition metal compound represented by Formula 1 may be represented by any one among the following Formulae 1-1 to 1-3:

[Formula 1-1]

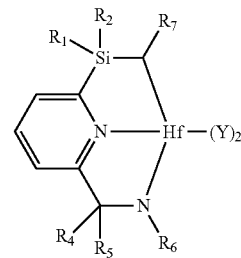

[Formula 1-2]

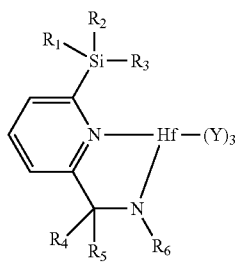

[Formula 1-3]

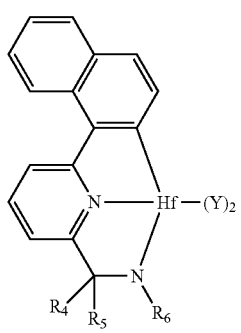

in Formulae 1-1 to 1-3, the definition of $R_1$ to $R_6$ is the same as described above, and R-7 is an alkyl group of 1 to 19 carbon atoms; an aryl group of 6 to 19 carbon atoms; or an arylalkyl group of 7 to 19 carbon atoms.

In addition, the transition metal compound represented by Formula 1 may be selected from the following compounds:

[Formula 1-1a]

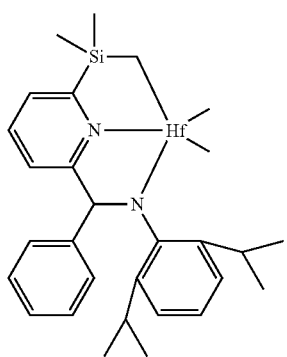

[Formula 1-1b]

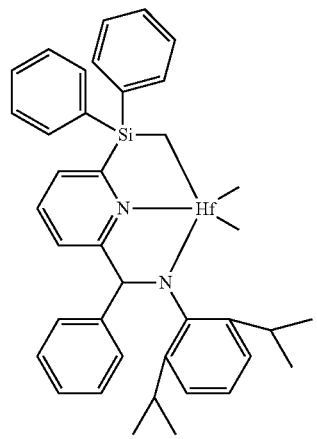

[Formula 1-2a]

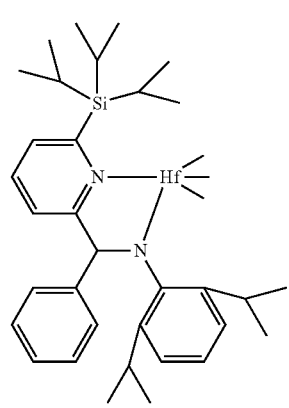

[Formula 1-3a]

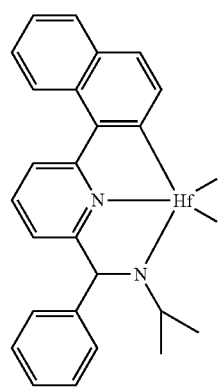

[Formula 1-3b]

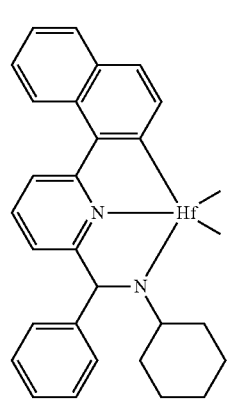

[Formula 1-3c]

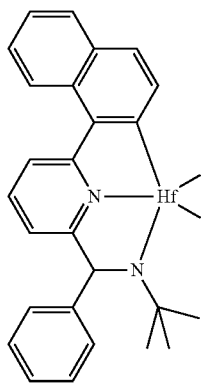

[Formula 1-3d]

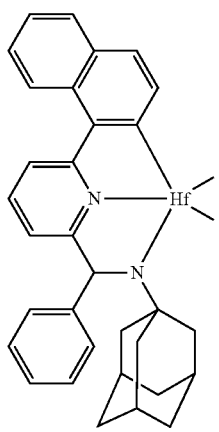

The transition metal compound represented by Formula 1 may be prepared from a ligand compound represented by the following Formula 2:

[Formula 2]

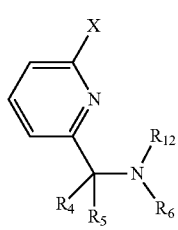

in Formula 2,

X is —Si($R_1$)($R_2$)($R_3$); or an aryl group of 6 to 20 carbon atoms, $R_1$ to $R_3$ are each independently an alkyl group of 1 to 20 carbon atoms; a cycloalkyl group of 3 to 20 carbon atoms; an aryl group of 6 to 20 carbon atoms; an alkylaryl group of 7 to 20 carbon atoms; or an arylalkyl group of 7 to 20 carbon atoms, $R_4$ and $R_5$ are each independently hydrogen; an alkyl group of 1 to 20 carbon atoms; an alkenyl group of 2 to 20 carbon atoms; an alkynyl group of 2 to 20 carbon atoms; a cycloalkyl group of 3 to 20 carbon atoms; an aryl group of 6 to 20 carbon atoms; an alkylaryl group of 7 to 20 carbon atoms; or an arylalkyl group of 7 to 20 carbon atoms, and $R_6$ is hydrogen; an alkyl group of 1 to 20 carbon atoms; a cycloalkyl group of 3 to 20 carbon atoms; an aryl group of 6 to 20 carbon atoms; an alkylaryl group of 7 to 20 carbon atoms; or an arylalkyl group of 7 to 20 carbon atoms, where if X is the aryl group of 6 to 20 carbon atoms, $R_6$ is not the aryl group of 6 to 20 carbon atoms or the alkylaryl group of 7 to 20 carbon atoms.

In addition, the ligand compound represented by Formula 2 may be represented by the following Formula 2-1 or 2-2:

[Formula 2-1]

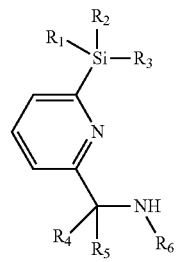

[Formula 2-2]

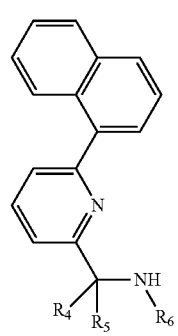

in Formulae 2-1 and 2-2, the definition of $R_1$ to $R_6$ are the same as described above for Formula 2.

In addition, the ligand compound represented by Formula 2 may particularly be selected from the following compounds:

[Formula 2-1a]

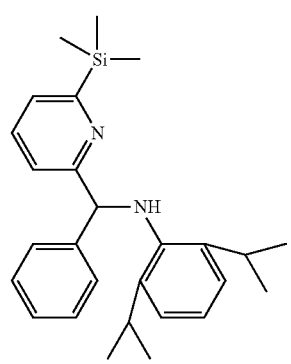

[Formula 2-1b]

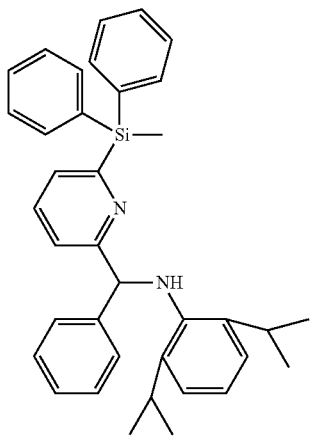

[Formula 2-2a]

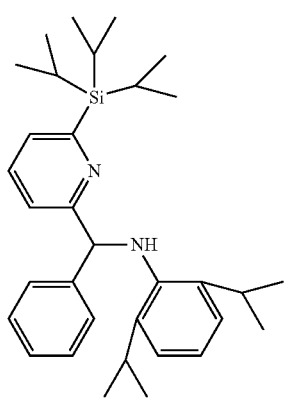

[Formula 2-3a]

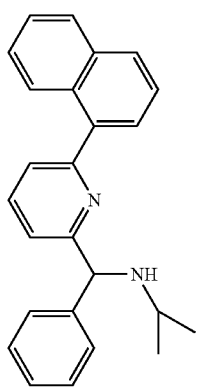

[Formula 2-3b]

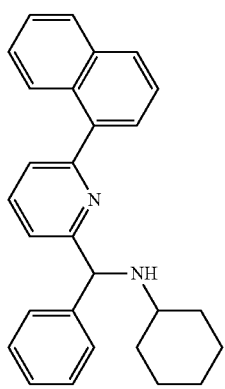

[Formula 2-3c]

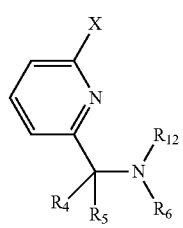

[Formula 2-3d]

The transition metal compound represented by Formula 1 of the present invention may be prepared by including a step of reacting the following ligand compound represented by Formula 2 and the following compound represented by Formula 3:

[Formula 2]

[Formula 3]

Hf(Y)₄

Meanwhile, the step of preparing a ligand compound according to the final structure of the transition metal compound represented by Formula 1 may be performed by the following Reaction 1 or Reaction 2:

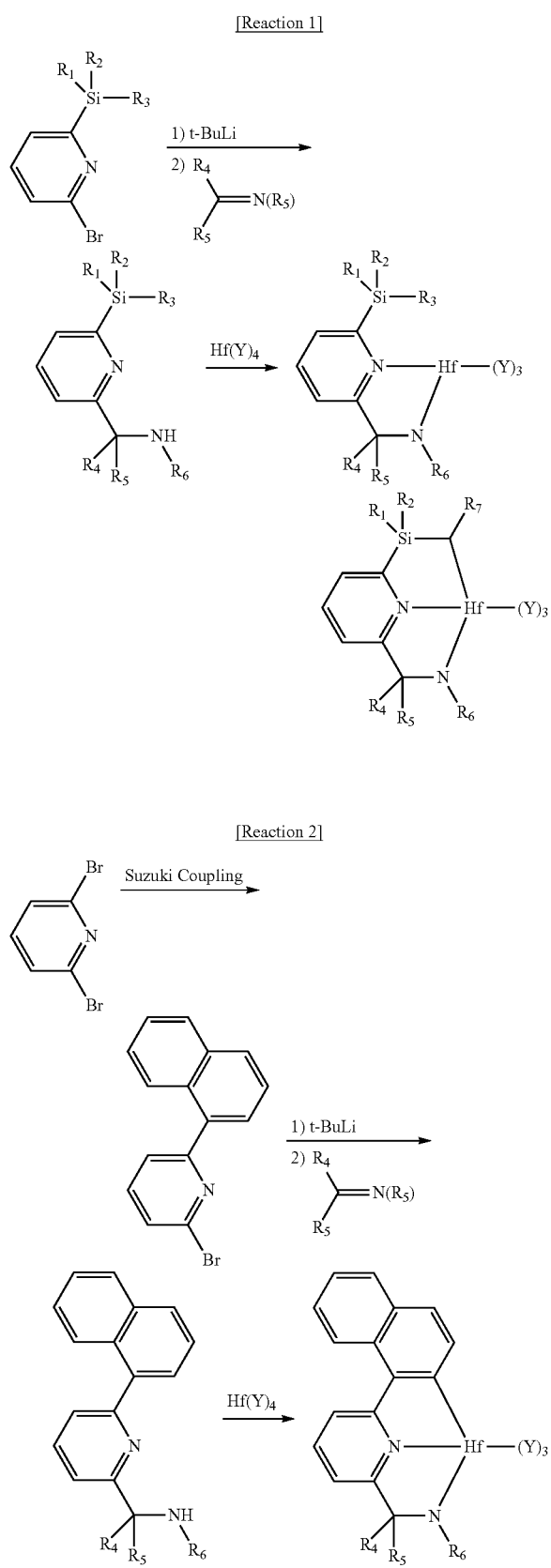

[Reaction 1]

[Reaction 2]

That is, the transition metal compound of Formula 1 may be prepared by introducing an aminoalkyl group to pyridine using an organolithium compound and an imine compound, and then, by introducing a transition metal through reacting with a transition metal compound, and particular reagent type, reaction temperature, pressure, etc. may be suitably changed considering the structure of a final compound, experimental conditions, etc., by a person skilled in the art.

In addition, the present invention provides a catalyst composition including the transition metal compound represented by Formula 1 and a cocatalyst. In the present invention, the term "composition" includes a mixture of materials included in the corresponding composition as well as a reaction product and decomposition product formed from the materials of the corresponding composition.

The cocatalyst may use any one well-known in the art, for example, one or more selected among the following Formulae 4 to 6:

$$—[Al(R_a)—O]_a—$$ [Formula 4]

$$D(R_a)_3$$ [Formula 5]

$$[L-H]^+[Z(A)_4]^- \text{ or } [L]^+[Z(A)_4]^-$$ [Formula 6]

where
each $R_a$ is independently a halogen radical; a hydrocarbyl radical of 1 to 20 carbon atoms; or a halogen-substituted hydrocarbyl radical of 1 to 20 carbon atoms,
a is an integer of 2 or more,
D is aluminum or boron,
L is a neutral or cationic Lewis acid,
Z is an element in group 13;
each A is independently an aryl group of 6 to 20 carbon atoms or an alkyl group of 1 to 20 carbon atoms, where one or more hydrogen atoms may be substituted with substituents; and
the substituent of A is a halogen group; a hydrocarbyl group of 1 to 20 carbon atoms; an alkoxy group of 1 to 20 carbon atoms; or an aryloxy group of 6 to 20 carbon atoms.

The compound represented by Formula 4 is not specifically limited as long as it is alkylaluminoxane. Preferable examples may include methylaluminoxane, ethylaluminoxane, isobutylaluminoxane, butylaluminoxane, etc., particularly preferably, methylaluminoxane.

The compound represented by Formula 5 is not specifically limited, and preferable examples thereof may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, etc., and more preferably, be selected from trimethylaluminum, triethylaluminum, and triisobutylaluminum.

Examples of the compound represented by Formula 6 may include dioctadecylmethylammonium tetrakispentafluorophenylborate [$(C_{18}H_{37})_2N(H)Me]^+[B(C_6F_5)_4]^-$, triethylammonium tetraphenylborare, tributylammonium tetraphenylborate, trimethylammonium tetraphenylborate, tripropylammonium tetraphenylborate, trimethylammonium tetra(p-tolyl)borate, trimethylammonium tetra(o,p-dimethylphenyl)borate, tributylammonium tetra(p-trifluoromethylphenyl)borate, trimethylammonium tetra(p-trifluoromethylphenyl)borate, tributylammonium tetrapentafluorophenylborate, N,N-diethylanilinium tetraphenylborate, N,N-diethylanilinium tetrapentafluorophenylborate, diethylammonium tetrapentafluorophenylborate, triphenylphosphonium tetraphenylborate, trimethylphosphonium tetraphenylborate, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra (p-trifluoromethylphenyl) aluminum, tributylammonium tetrapentafluorophenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, tripropylammonium tetra (p-tolyl) borate, triethylammonium tetra(o,p-dimethylphenyl)borate, triphenylcarbonium tetra(p-trifluoromethylphenyl)borate, triphenylcarbonium tetrapentafluorophenylborate, etc.

As the reaction solvent used during the preparation of the composition, a hydrocarbon solvent such as pentane, hexane and heptane, or an aromatic solvent such as benzene and toluene may be used, but the present invention is not limited thereto, and all solvents used in this technical field may be used.

In addition, the transition metal compound of Formula 1 and the cocatalyst may be used in a supported type by a support. Silica or alumina may be used as the support.

In addition, the present invention provides a method for preparing an olefin polymer including a step of polymerizing an olefin monomer in the presence of the catalyst composition.

In the present invention, the term "polymer" refers to a polymer compound prepared by polymerizing monomers of the same or different types. Such a general term of polymer includes the term of homopolymer used for referring to a polymer prepared from only one type of monomer and the term of interpolymer specified as follows.

In the present invention, the term "interpolymer" refers to a polymer prepared by polymerizing at least two different types of monomers. Like this, a general term of interpolymer refers to a polymer prepared from two different types of monomers and includes a commonly used copolymer and a polymer prepared from two or more different types of monomers.

In the present invention, the olefin monomer may be one or more selected from the group consisting of ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene and 1-eicosene, without limitation.

Particularly, the olefin polymer of the present invention may be an olefin homopolymer, or an olefin-alpha-olefin copolymer according to the type of the olefin monomer, and preferably, may be an ethylene/alpha-olefin copolymer. In this case, the amount of the alpha-olefin monomer, which is a comonomer, may be suitably selected according to the use, purpose, etc., of the olefin polymer by a person skilled in the art, and may be about 1 to 99 mol %.

The catalyst composition may be injected after being dissolved or diluted in an aliphatic hydrocarbon solvent of 5 to 12 carbon atoms such as pentane, hexane, heptane, nonane, decane, isomers thereof, an aromatic hydrocarbon solvent such as toluene and benzene, or a hydrocarbon solvent substituted with a chlorine atom such as dichloromethane and chlorobenzene, which are suitable for an olefin polymerization process. The solvent used may preferably be used after removing a small amount of water or air, which functions as a catalyst poison, by treating with a small amount of alkylaluminum, and may be treated by further using a cocatalyst.

The most preferable preparation process using the catalyst composition is a solution process, and if the composition is used together with an inorganic support such as silica, it may also be applied to a slurry process or a gas phase process.

The polymerization may be performed by homopolymerizing one type of olefin monomer or copolymerizing two or more olefin monomers by using one of a continuous slurry polymerization reactor, a roof slurry reactor, a gas phase reactor, or a solution reactor.

In addition, to remove moisture in the reactor during performing polymerization reaction, an organoaluminum compound may be further injected, and the polymerization reaction may be performed in the presence thereof. Particular examples of such organoaluminum compound may include trialkylaluminum, dialkylaluminum halide, alkylaluminum dihalide, aluminum dialkyl hydride or alkyl aluminum sesquihalide, and more particular examples thereof may include $Al(C_2H_5)_3$, $Al(C_2H_5)_2H$, $Al(C_3H_7)_3$, $Al(C_3H_7)_2H$, $Al(i-C_4H_9)_2H$, $Al(C_8H_{17})_3$, $Al(C_{12}H_{25})_3$, $Al(C_2H_5)(C_{12}H_{25})_2$, $Al (i-C_4H_9)(C_{12}H_{25})_2$, $Al(i-C_4H_9)_2H$, $Al(i-C_4H_9)_3$, $(C_2H_5)_2AlCl$, $(i-C_3H_9)_2AlCl$ or $(C_2H_5)_3Al_2Cl_3$. Such an organoaluminum compound may be continuously injected to the reactor, or may be injected in a ratio of about 0.1 to 10 mol per 1 kg of a reaction medium which is injected to the reactor for suitable removal of moisture.

According to an embodiment of the present invention, the polymerization of the olefin polymer may be performed under conditions of a temperature of about 60 to 200° C., particularly, a temperature of about 70 to 150° C., or a temperature of about 80 to 100° C., and a pressure of about 10 to 100 bar, particularly, a pressure of about 15 to 50 bar, or a pressure of about 20 to 40 bar, for about 8 minutes to 2 hours.

EXAMPLES

Hereinafter, the present invention will be explained in more detail referring to the examples. However, the examples are for illustrating the present invention, and the scope of the present invention is not limited thereto.

[Reagents and Experimental Conditions]

All experiments were performed under an inert atmosphere using a standard glove box and Schlenk technique. Toluene, hexane, diethyl ether, THF and C6D6 were used after distillation from benzophenone ketyl. Methylcyclohexane (anhydrous grade) used in polymerization reaction was used after purchasing from Tokyo Chemical Industry (TCI) and purifying using a Na/K alloy. Ethylene was used after purifying by contacting with a molecular sieve and copper under a pressure of 50 bar.

$^1$H NMR (600 MHz) and $^{13}$C NMR (150 MHz) spectrums were recorded using a ECZ 600 apparatus (JOEL).

2-bromo-6-(trimethylsilyl)pyridine was prepared by a method disclosed in a document [J. Chem. Soc., Perkin Trans. 1 2002, 1858-1868], 2-bromo-6-(triisopropylsilyl)pyridine was prepared by a method disclosed in a document [Tetrahedron Lett. 1998, 39, 6151-6154], 2-bromo-6-(naphthalene-1-yl)pyridine was prepared by a method disclosed in a document [RSC Adv. 2015, 5, 53073-53085], 2-iPrC$_6$H$_4$Li was prepared by a method disclosed in a document [J. C. U.S. Patent Appl. 0220050 A1(2004)], and PhC(H)=NCH(CH$_3$)$_2$ was prepared by a method disclosed in a document [Chem. Eur. J. 2017, 23, 10997-11000].

Synthesis of Transition Metal Compounds

Preparation Example 1: Formula 1-1a (1) Ligand Compound

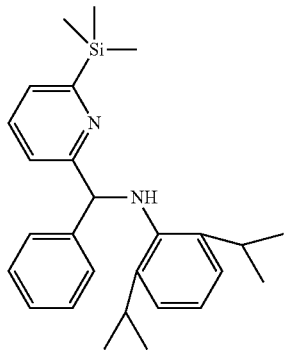

[Formula 2-1a]

Figure 1B:
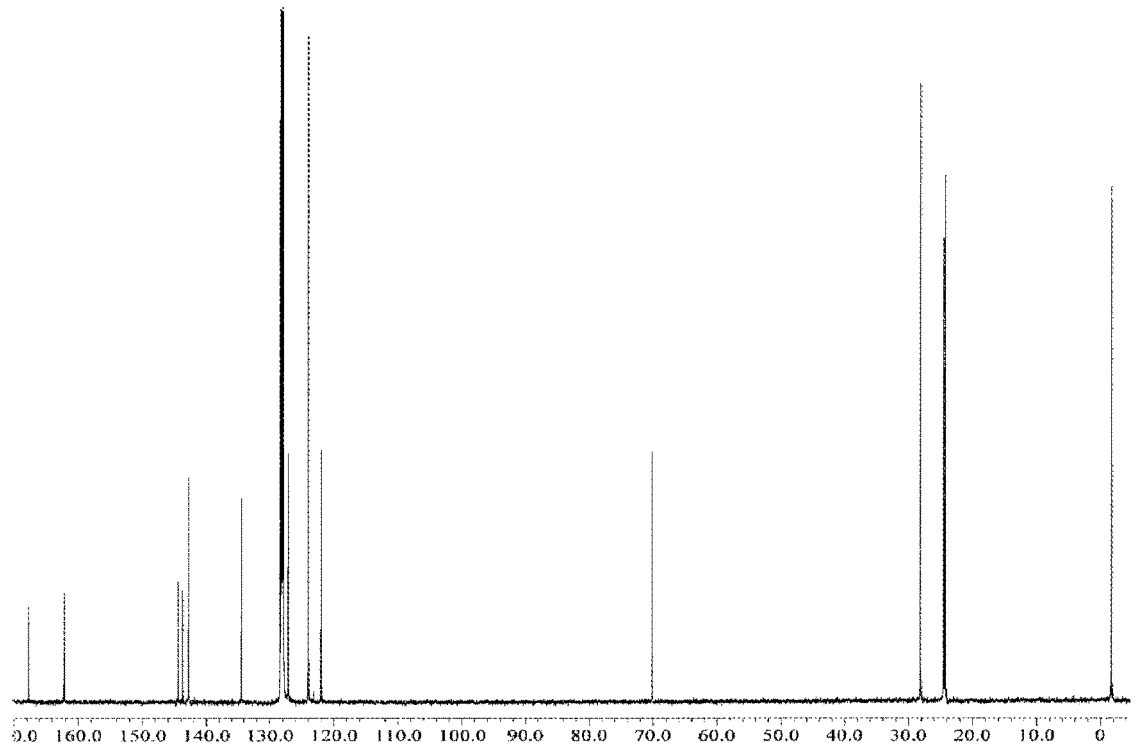

To a solution of 2-bromo-6-(trimethylsilyl)pyridine (0.735 g, 3.19 mmol) in THF (15 mL), a tBuLi solution (3.76 mL, 6.39 mmol, 1.7 M in pentane) in hexane (4 mL) was added at −78° C., and stirred for 2 hours. A solution of PhC(H)=N(2,6-iPr$_2$C$_6$H$_3$) (0.763 g, 2.87 mmol) in THF (15 mL) was added thereto. After stirring for 3 hours, the solution thus produced was slowly heated to room temperature and stirred overnight. Water (30 mL) was added, and the resultant product was extracted with ethyl acetate (3×20 mL). Organic phases were collected and dried on an anhydrous MgSO$_4$ phase, and solvents were removed by a rotary evaporator. Through separating by silica gel column chromatography using hexane and toluene (2:1 v/v), a pale yellow oil was obtained (0.934 mg, 78%). The results are shown in FIGS. 1A-B.

$^1$H NMR (600 MHz, C$_6$D$_6$): δ 7.50 (d, J=7.8 Hz, 2H), 7.15-7.02 (m, 6H), 7.00 (t, J=7.8 Hz, 1H), 6.93 (t, J=7.8 Hz, 1H), 6.66 (d, J=6.6 Hz, 1H), 5.69 (br s, 1H, NH), 5.24 (s, 1H, NCH), 3.44 (sept, J=6.6 Hz, 2H, CH(CH$_3$)$_2$), ), 1.19 (d, J=7.2 Hz, 6H, CH(CH$_3$)$_2$), 1.09 (d, J=7.2 Hz, 6H, CH(CH$_3$)$_2$), 0.30 (s, 9H, CH$_3$) ppm.

$^{13}$C{$^1$H} NMR (150 MHz, C$_6$D$_6$): δ−1.76, 24.28, 28.13, 70.17, 121.96, 123.97, 127.07, 127.13, 128.40, 134.42, 142.80, 143.71, 144.39, 162.14, 167.69 ppm.

IR (neat): ν 3361 (N—H) cm$^{-1}$.

HRMS (EI): m/z calcd ([M$^+$] C$_{27}$H$_{36}$N$_2$Si) 416.2648. Found: 416.2650.

(2) Transition Metal Compound

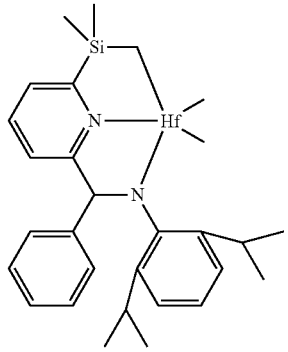

[Formula 1-1a]

To a solution of HfCl$_4$ (0.230 g, 0.718 mmol) in toluene (2 mL), MeMgBr (1.00 mL, 2.94 mmol, 3.0 M solution in diethyl ether) was added dropwisely at −78° C. The resultant solution was stirred at −40 to −35° C. for 1 hour to precipitate a white solid. After cooling to −78° C., a solution of the ligand compound (0.230 g, 0.552 mmol) in toluene was added drowisely.

The mixture thus obtained was stirred at −40 to −35° C. for 2 hours, and slowly heated to room temperature. After stirring overnight, all volatile materials were removed using a vacuum line. Toluene (10 mL) was added, and the product was extracted, filtered on celite, and collected. After removing solvents, the residue was pulverized with hexane to obtain a yellow oil (0.220 g, 60%).

Figure 2A:
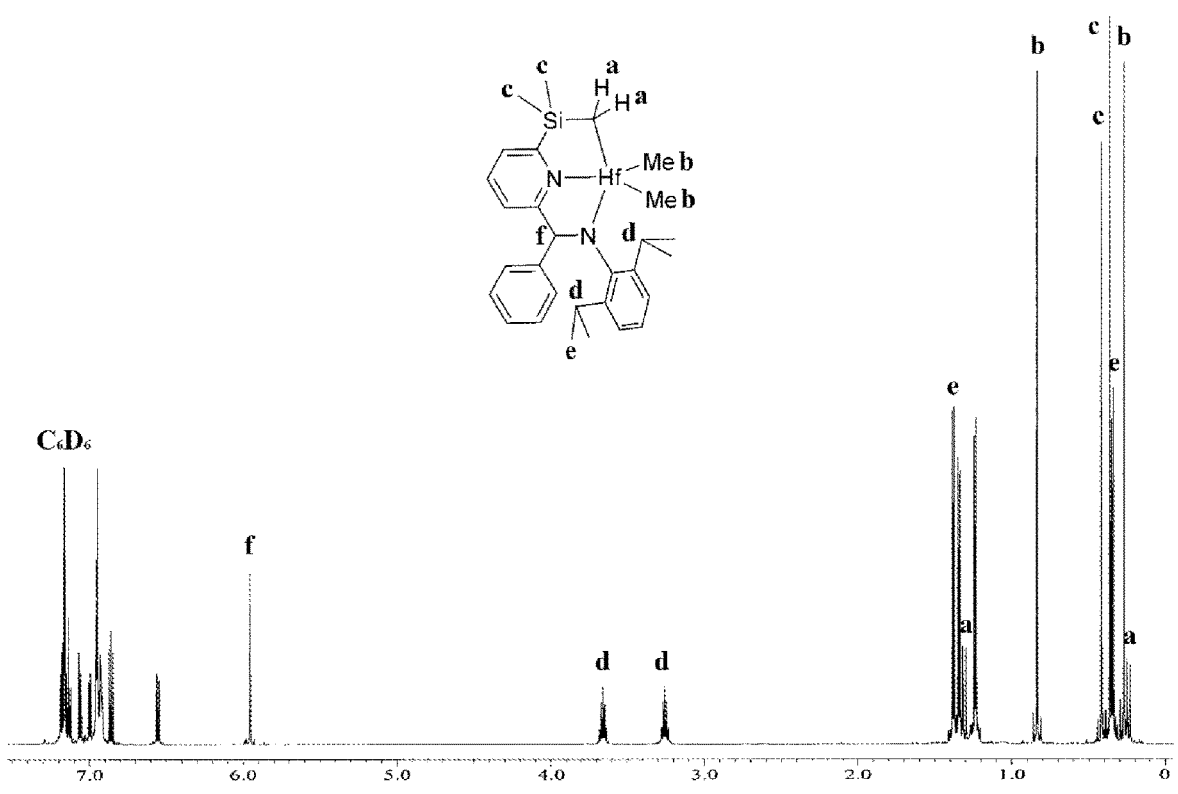
Figure 2B:
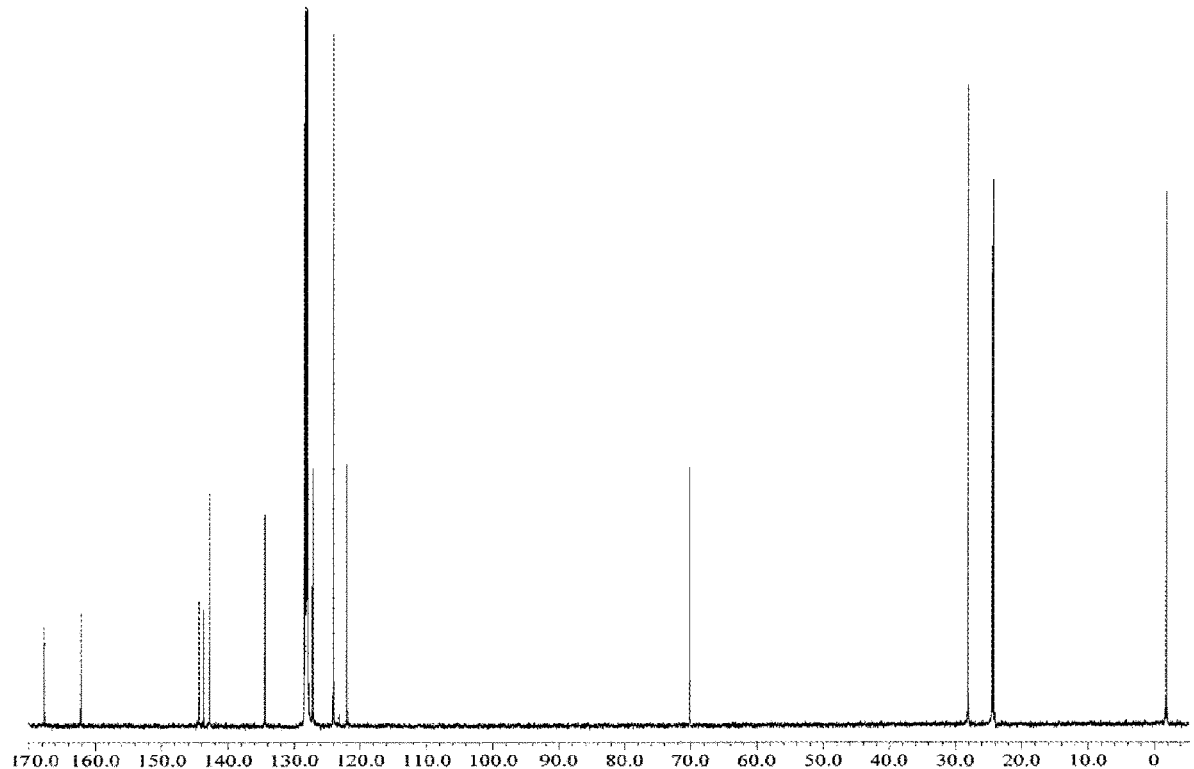

After separating, the product thus obtained was brought into contact with a chloromethyl-Hf compound and treated with MeLi in toluene to obtain a hafnium compound. $^1$H and $^{13}$C NMR spectrums are shown in FIGS. 2A-B.

$^1$H NMR (600 MHz, C$_6$D$_6$): δ 7.21-7.11 (m, 2H), 7.06 ((d, J=7.2 Hz, 1H), 7.00 ((d, J=7.8 Hz, 1H), 6.98-6.90 (m, 5H), 6.86 (t, J=7.2 Hz, 1H), 6.55 ((d, J=9.0 Hz, 1H), 5.96 (s, 1H, NCH), 3.66 (sept, J=6.6 Hz, 1H, CH(CH$_3$)$_2$), 3.26 (sept, J=6.6 Hz, 1H, CH(CH$_3$)$_2$), 1.38 ((d, J=7.2 Hz, 3H, CH(CH$_3$)$_2$), 1.34 ((d, J=7.2 Hz, 3H, CH(CH$_3$)$_2$), 1.31 ((d, J=12.6 Hz, 1H, SiCH$_2$Hf), 1.24 ((d, J=7.2 Hz, 3H, CH(CH$_3$)$_2$), 0.84 (s, 3H, SiCH$_3$), 0.42 (s, 3H, HfCH$_3$), 0.37 (s, 3H, SiCH$_3$), 0.35 ((d, J=7.2 Hz, 3H, CH(CH$_3$)$_2$), 0.27 (s, 3H, HfCH$_3$), 0.24 ((d, J=12.6 Hz, 1H, SiCH$_2$Hf) ppm.

$^{13}$C{$^1$H} NMR (150 MHz, C$_6$D$_6$): δ 11.17, 18.70, 24.09, 24.38, 28.00, 69.90, 121.38, 123.77, 123.96, 126.87, 129.14, 133.86, 142.84, 143.84, 161.94, 164.65 ppm.

Preparation Example 2: Formula 1-1b (1) Preparation of 2-bromo-6-(methyldiphenylsilyl)pyridine To a solution of 2,6-dibromopyridine (1.00 g, 4.22 mmol) in diethyl ether (20 mL), nBuLi (1.70 mL, 4.22 mmol, 2.5 M solution in hexane) was added at −78° C. The solution thus obtained was heated to −40° C. and stirred for 20 minutes. After cooling to −78° C., Ph$_2$MeSiCl (1.08 g, 4.64 mmol) in diethyl ether (5 mL) was added thereto. After stirring for 3 hours, the solution was heated to room temperature, water (30 mL) was added, and the product was extracted with diethyl ether (3×10 mL). An organic phase thus collected was dried on an anhydrous $MgSO_4$ phase, and solvents were removed by a rotary evaporator. Through separating the product by silica gel column chromatography using hexane and ethyl acetate (50:1 v/v), a white solid was obtained (1.05 g, 70%).

$^1$H NMR (600 MHz, $C_6D_6$): δ 7.58 (d, J=7.2 Hz, 4H), 7.20-7.12 (m, 6H), 7.04 (d, J=7.2 Hz, 1H), 6.91 (d, J=7.8 Hz, 1H), 6.53 (t, J=7.2 Hz, 1H), 0.82 (s, 3H, $CH_3$) ppm.

$^{13}$C{$^1$H} NMR (150 MHz, $C_6D_6$): δ−3.92, 127.74, 128.34, 129.98, 135.17, 135.71, 136.54, 144.07, 167.94 ppm.

IR (neat): n 478 (C—Br) $cm^{-1}$.

HRMS (FAB): m/z calcd ([M+H]$^+$ $C_{18}H_{16}BrNSi$) 354.0314. Found: 354.0310.

(2) Ligand Compound

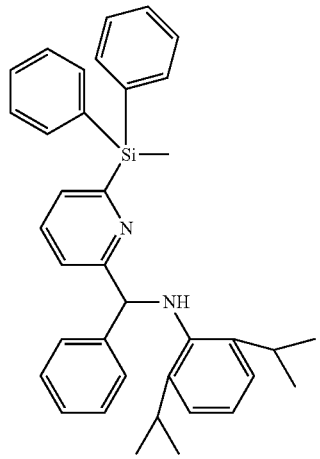

[Formula 2-1b]

The same method for preparing [Formula 2-1a] was performed using tBuLi (1.66 mL, 2.82 mmol, 1.7 M in pentane), 2-bromo-6-(methyldiphenylsilyl)pyridine (0.500 g, 1.41 mmol), and PhC(H)=N (2,6-iPr$_2$C$_6$H$_3$) (0.337 g, 1.27 mmol).

Figure 3A:
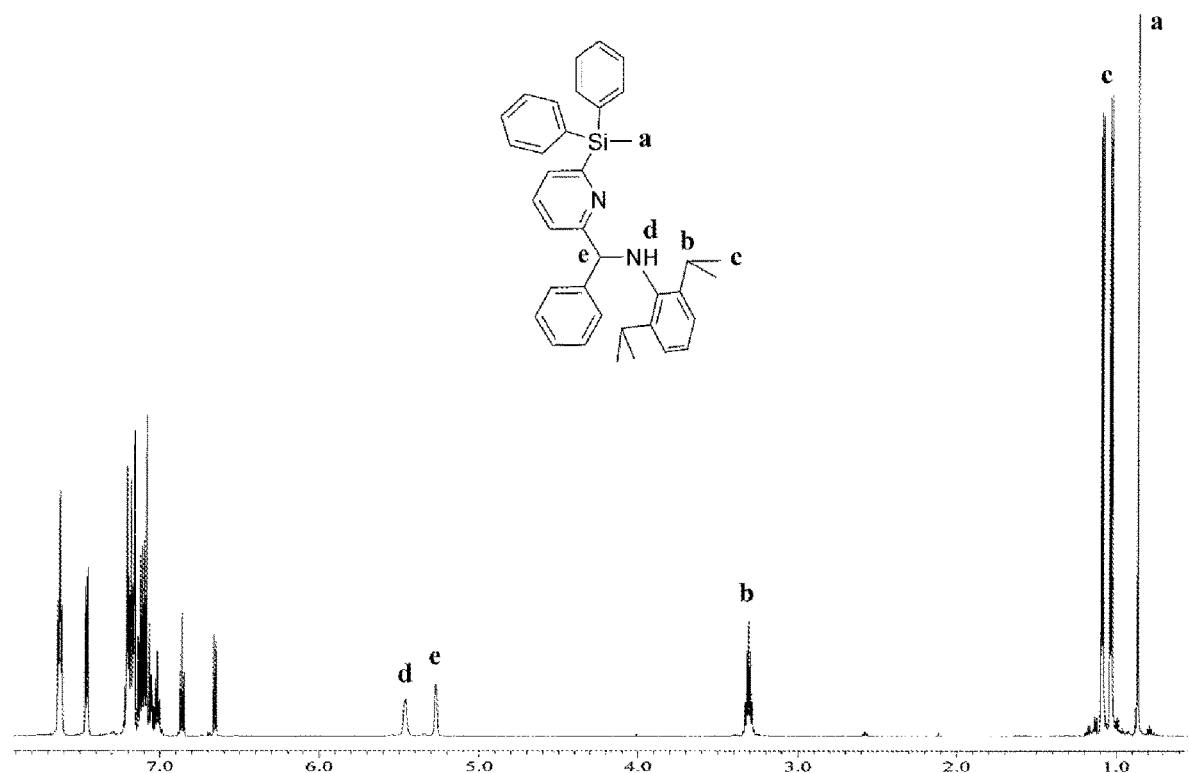
FIG. 3A shows a $^1$H NMR spectrum of the ligand compound of 2-1b.
Figure 3B:
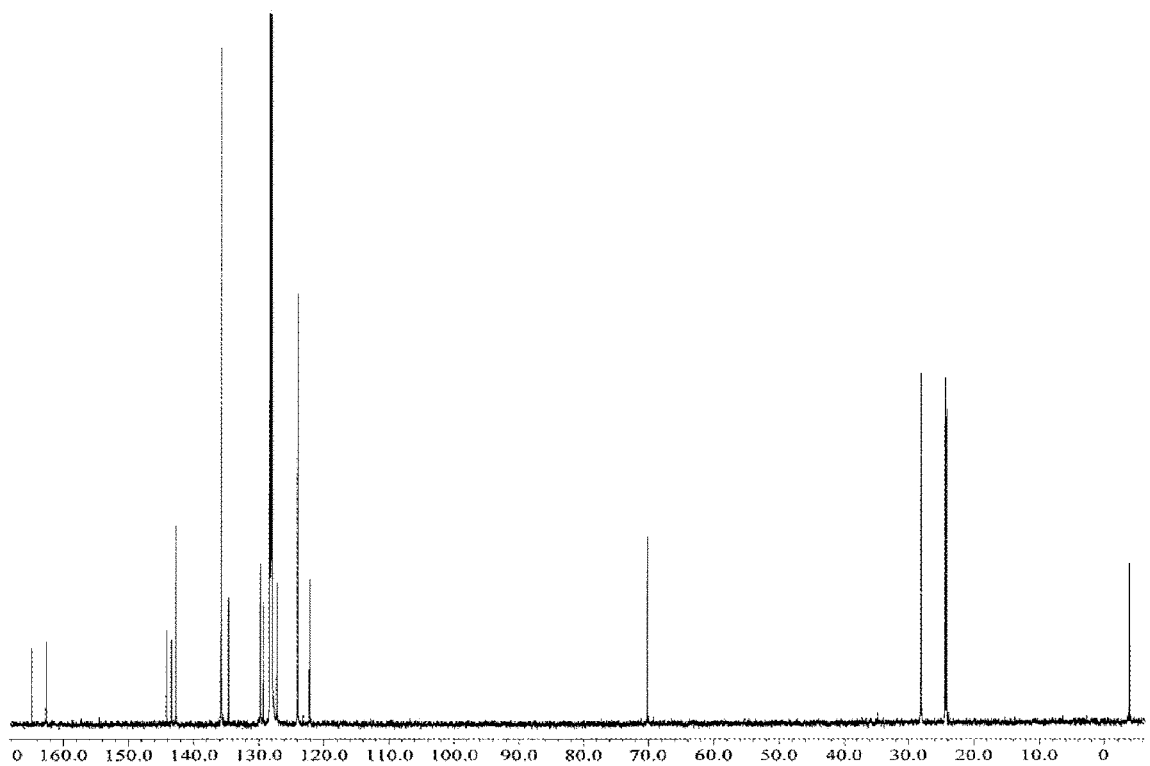
FIG. 3B shows a $^{13}$C NMR spectrum of the ligand compound of 2-1b.

Through separating by silica gel chromatography using hexane and toluene (2:1 v/v), a white glassy solid (0.186 g, 27%) was obtained. The results are shown in FIGS. 3A-B.

$^1$H NMR (600 MHz, $C_6D_6$): δ 7.63 (t, J=7.8 Hz, 4H), 7.46 (d, J=7.2 Hz, 2H), 7.22-7.00 (m, 13H), 6.86 (t, J=7.2 Hz, 1H), 6.66 (d, J=7.2 Hz, 1H), 5.52-5.40 (br, 1H, NH), 5.32-5.20 (br, 1H, NCH), 3.31 (sept, J=6.0 Hz, 2H, CH(CH$_3$)$_2$), 1.35 (d, J=6.6 Hz, 6H, CH(CH$_3$)$_2$), 1.09 (d, J=6.6 Hz, 6H, CH(CH$_3$)$_2$), 0.87 (s, 3H, CH$_3$) ppm.

$^{13}$C{$^1$H} NMR (150 MHz, $C_6D_6$): δ−3.83, 24.20, 24.45, 28.13, 122.14, 123.94, 127.11, 128.26, 128.42, 129.31, 129.76, 129.81, 134.66, 135.79, 142.72, 143.43, 144.14, 162.61, 164.85 ppm.

IR (neat): v 3361 (N—H) $cm^{-1}$.

HRMS (EI): m/z calcd ([M$^+$] $C_{37}H_{40}N_2Si$) 540.2961. Found: 540.2964.

(3) Transition Metal Compound

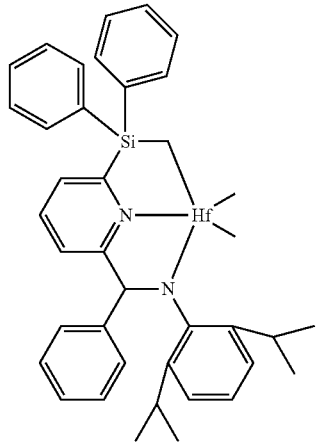

[Formula 1-1b]

Figure 4A:
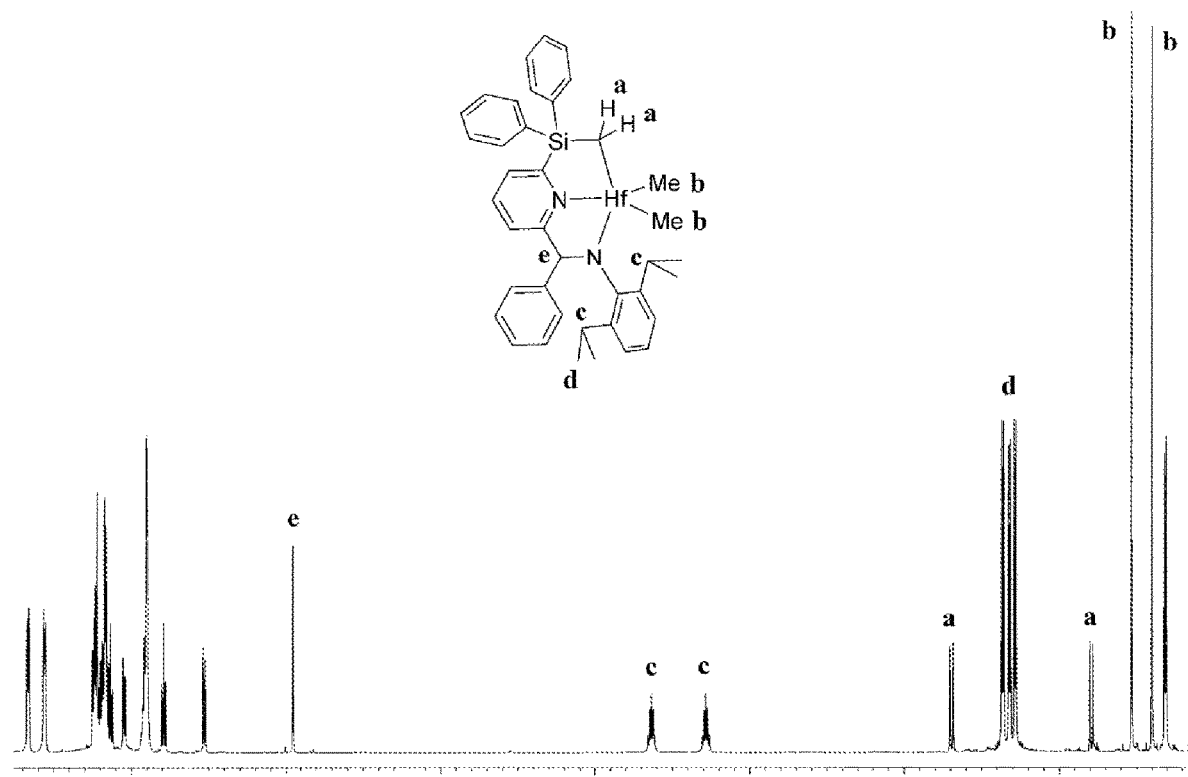
FIG. 4A shows a $^1$H NMR spectrum of the transition metal compound of 1-1b.
Figure 4B:
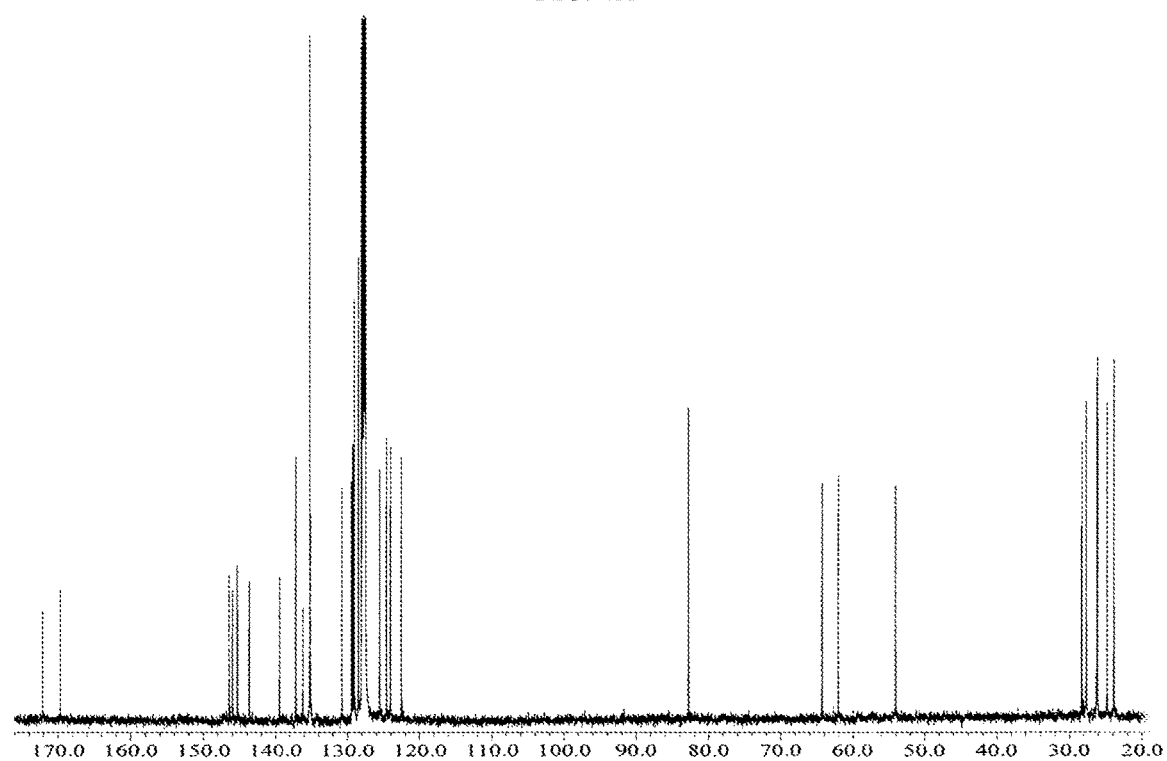
FIG. 4B shows a $^{13}$C NMR spectrum of the transition metal compound of 1-1b.

By using HfCl$_4$ (0.155 g, 0.483 mmol), MeMgBr (0.70 mL, 2.0 mmol, 3.0 M solution in diethyl ether) and the [Formula 2-1b] compound (0.174 g, 0.322 mmol) and performing the same method for preparing [Formula 1-1a], an orange glassy solid (0.169 g, 84%) was obtained. $^1$H and $^{13}$C NMR spectrums are shown in FIGS. 4A-B.

$^1$H NMR (600 MHz, $C_6D_6$): δ 7.66 (d, J=5.4 Hz, 2H), 7.61-7.52 (m, 2H), 7.27-7.11 (m, 9H), 7.04 (d, J=7.8 Hz, 1H), 6.95-6.86 (m, 5H), 6.79 (t, J=7.2 Hz, 1H), 6.53 (d, J=8.4 Hz, 1H), 5.95 (s, 1H, NCH), 3.64 (sept, J=6.6 Hz, 1H, CH(CH$_3$)$_2$), 3.29 (sept, J=6.6 Hz, 1H, CH(CH$_3$)$_2$), 1.69 (d, J=13.2 Hz, 1H, SiCH$_2$Hf), 1.36 (d, J=7.2 Hz, 3H, CH(CH$_3$)$_2$), 1.32 (d, J=7.2 Hz, 3H, CH(CH$_3$)$_2$), 1.28 (d, J=7.2 Hz, 3H, CH(CH$_3$)$_2$), 0.79 (d, J=13.2 Hz, 3H, SiCH$_2$Hf), 0.53 (s, 3H, HfCH$_3$), 0.40 (s, 3H, HfCH$_3$), 0.31 (d, J=7.2 Hz, 3H, CH(CH$_3$)$_2$) ppm.

$^{13}$C{$^1$H} NMR (150 MHz, $C_6D_6$): δ 24.22, 25.19, 26.45, 26.59, 28.04, 28.64, 54.40, 62.43, 64.65, 83.14, 127.82, 128.28, 128.40, 128.83, 129.43, 129.62, 129.77, 131.11, 135.49, 135.52, 136.58, 137.46, 139.82, 144.12, 145.66, 146.34, 146.82, 170.02, 172.44 ppm. Anal. Calcd. ($C_{39}H_{44}N_2SiHf$): C, 62.68; H, 5.93; N, 3.75%. Found: C, 62.73; H, 5.97; N, 3.80%.

Preparation Example 3: Formula 1-2a (1) Ligand Compound

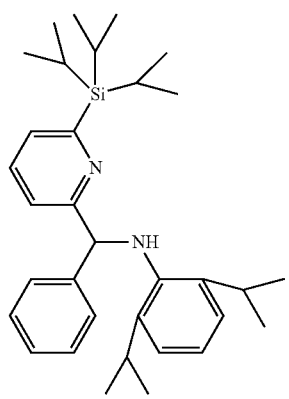

[Formula 2-2a]

The same method for preparing [Formula 2-1a] was performed using tBuLi (0.56 mL, 0.954 mmol, 1.7 M in pentane), 2-bromo-6-(triisopropylsilyl)pyridine (0.150 g, 0.477 mmol), and PhC(H)=N (2,6-iPr$_2$C$_6$H$_3$) (0.114 g, 0.429 mmol).

Figure 5A:
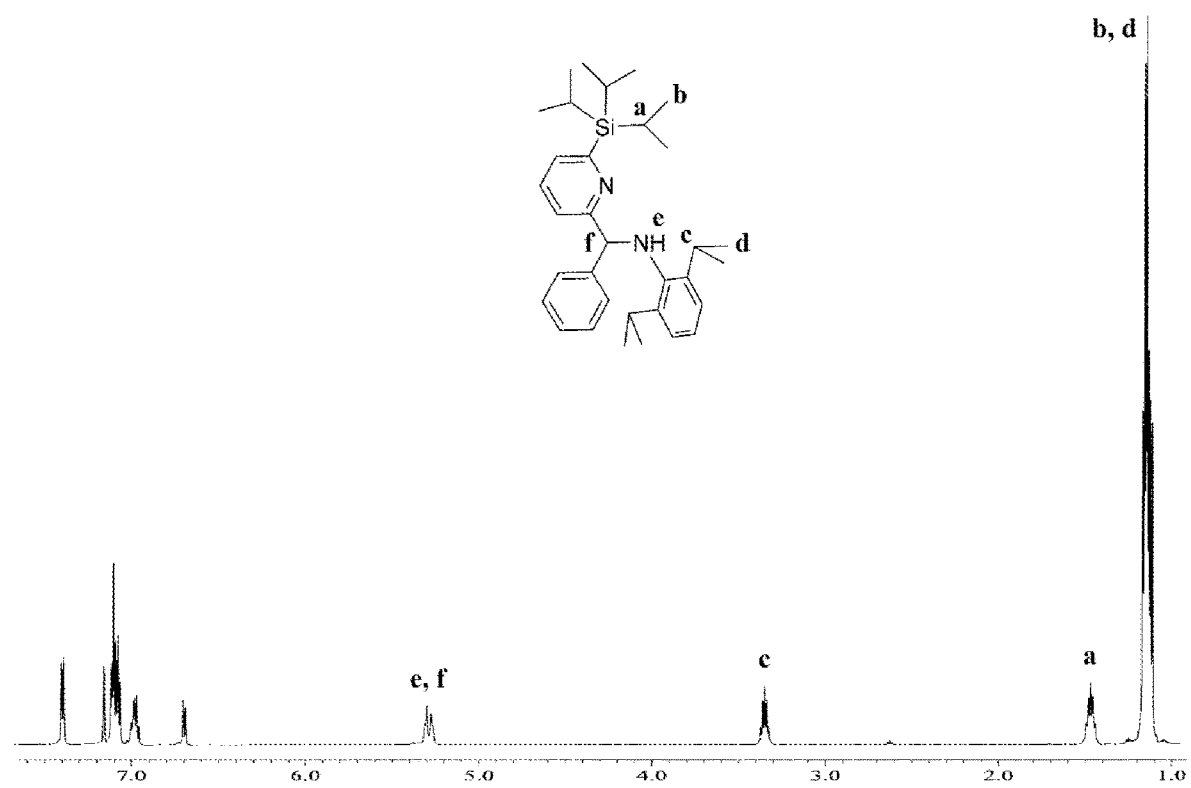
Figure 5B:
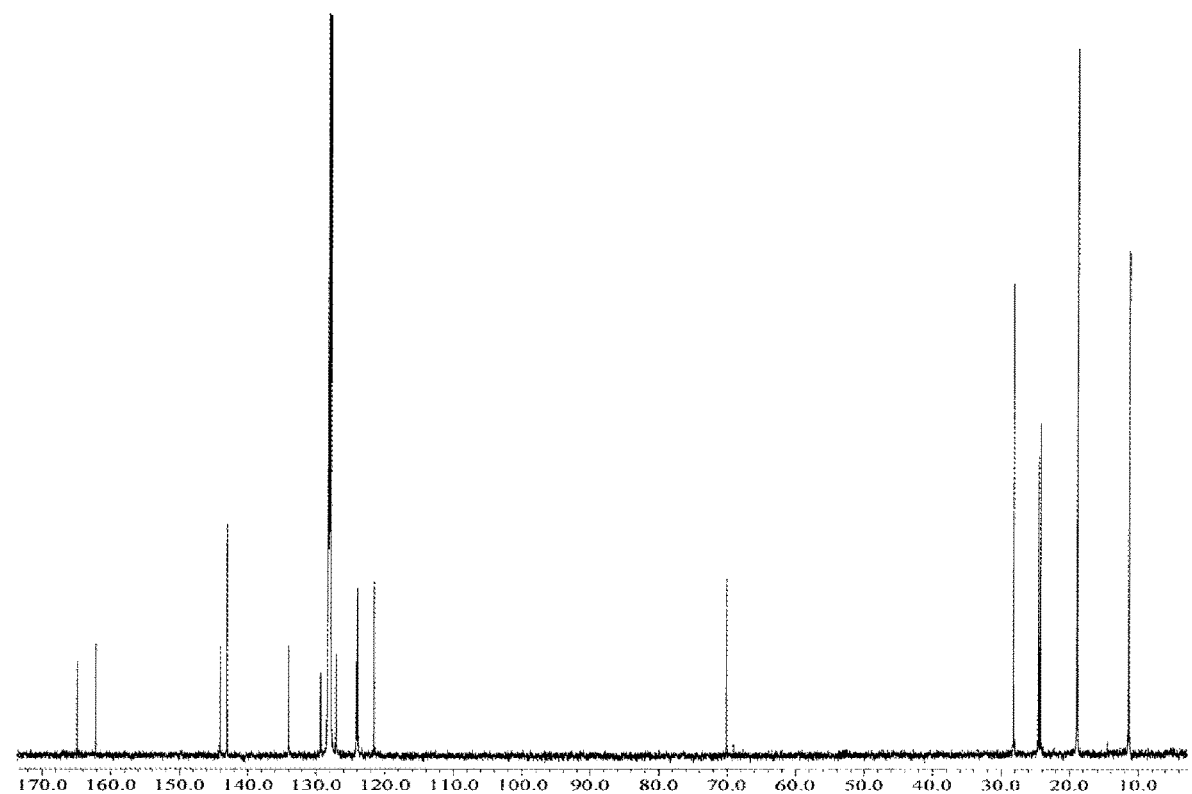

Through separating by silica gel chromatography using hexane and toluene (2:1 v/v), a pale yellow oil (0.161 g, 75%) was obtained. $^1$H and $^{13}$C NMR spectrums are shown in FIGS. 5A-B.

$^1$H NMR (600 MHz, C$_6$D$_6$): δ 7.40 (d, J=7.2 Hz, 2H), 7.15-7.05 (m, 6H), 7.22-7.00 (m, 2H), 6.70 (d, J=8.4 Hz, 1H), 5.34-5.21 (br, 2H, NH, NCH), 3.35 (sept, J=7.2 Hz, 2H, CH(CH$_3$)$_2$), 1.47 (sept, J=7.2 Hz, 3H, SiCH(CH$_3$)$_2$), 1.20-1.10 (m, 30H, CH(CH$_3$)$_2$, SiCH(CH$_3$)$_2$) ppm.

$^{13}$C{$^1$H} NMR (150 MHz, C$_6$D$_6$): δ 11.17, 18.70, 24.09, 24.38, 28.00, 69.90, 121.38, 123.77, 123.96, 126.87, 129.14, 133.86, 142.84, 143.84, 161.94, 164.65 ppm.

IR (neat): ν 3366 (N—H) cm$^{-1}$.

HRMS (EI): m/z calcd ([M$^+$] C$_{33}$H$_{48}$N$_2$Si) 500.3587. Found: 500.3589.

(2) Transition Metal Compound

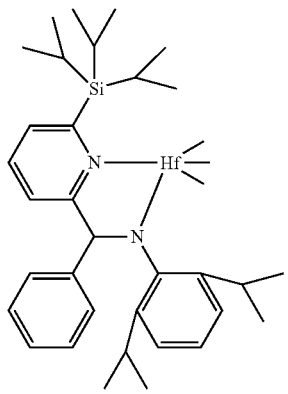

[Formula 1-2a]

Figure 6A:
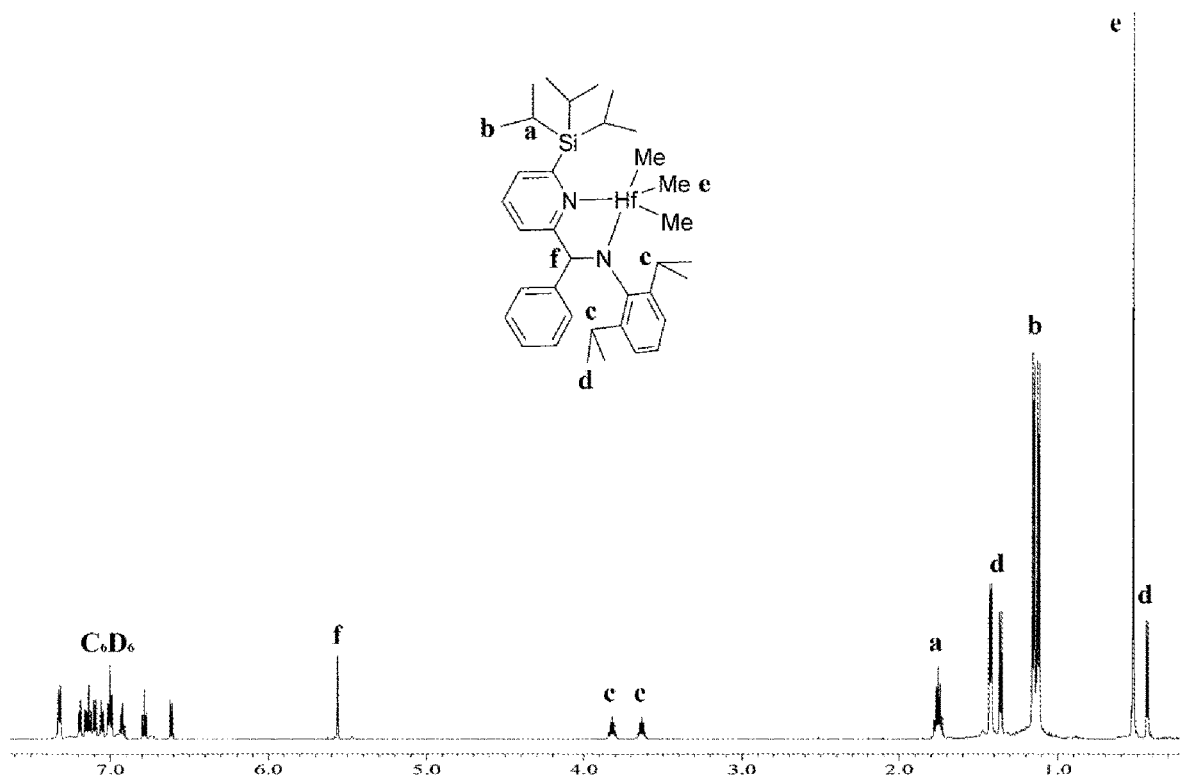
Figure 6B:
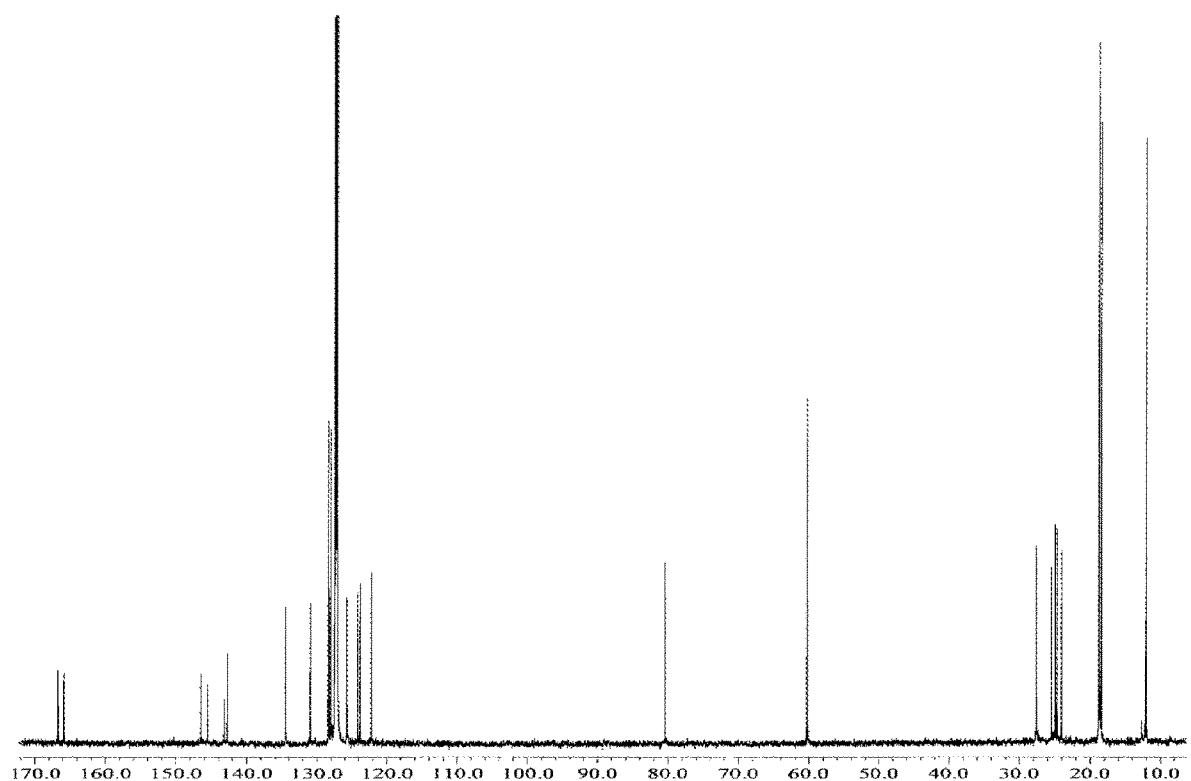

By using HfCl$_4$ (0.071 g, 0.22 mmol), MeMgBr (0.30 mL, 0.91 mmol, 3.0 M solution in diethyl ether) and the [Formula 2-2a] compound (0.074 g, 0.15 mmol) and performing the same method for preparing [Formula 1-1a], a yellow oil (0.097 g, 91%) was obtained. $^1$H and $^{13}$C NMR spectrums are shown in FIGS. 6A-B.

$^1$H NMR (600 MHz, C$_6$D$_6$): δ 7.32 (d, J=7.8 Hz, 2H), 7.19 (d, J=7.8 Hz, 1H), 7.14 (t, J=7.8 Hz, 1H), 7.10 (d, J=7.8 Hz, 1H), 7.05 (d, J=7.2 Hz, 1H), 7.00 (t, J=7.2 Hz, 2H), 6.92 (t, J=7.2 Hz, 1H), 6.79 (t, J=7.2 Hz, 1H), 6.10 (d, J=7.8 Hz, 1H), 5.56 (s, 1H, NCH), 3.82 (sept, J=6.6 Hz, 1H, CH(CH$_3$)$_2$), 3.63 (sept, J=6.6 Hz, 1H, CH(CH$_3$)$_2$), 1.76 (sept, J=7.2 Hz, 3H, SiCH(CH$_3$)$_2$), 1.43 (d, J=7.2 Hz, 3H, CH(CH$_3$)$_2$), 1.42 (d, J=6.6 Hz, 3H, CH(CH$_3$)$_2$), 1.36 (d, J=6.6 Hz, 3H, CH(CH$_3$)$_2$), 1.15 (d, J=7.8 Hz, 9H, SiCH(CH$_3$)$_2$), 1.12 (d, J=7.2 Hz, 9H, SiCH(CH$_3$)$_2$), 0.52 (s, 9H, Hf(CH$_3$)$_3$), 0.43 (d, J=7.8 Hz, 3H, CH(CH$_3$)$_2$) ppm.

$^{13}$C{$^1$H} NMR (150 MHz, C$_6$D$_6$): δ 12.90, 19.25, 19.56, 24.86, 25.45, 25.73, 26.24, 28.38, 28.41, 61.07, 81.25, 123.02, 124.64, 125.02, 126.54, 127.98, 128.86, 129.18, 131.71, 135.31, 143.56, 144.00, 146.32, 147.25 ppm.

Preparation Example 4: Formula 1-3a (1) Ligand Compound

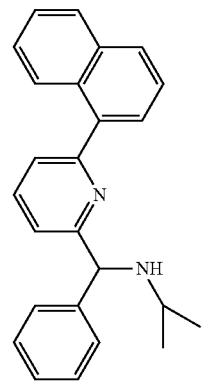

[Formula 2-3a]

The same method for preparing [Formula 2-1a] was performed using tBuLi (0.79 mL, 1.34 mmol, 1.7 M in pentane), 2-bromo-6-(naphthalene-1-yl) pyridine (0.190 g, 0.669 mmol), and PhC(H)=NCH(CH$_3$)$_2$ (0.108 g, 0.736 mmol).

Figure 7A:
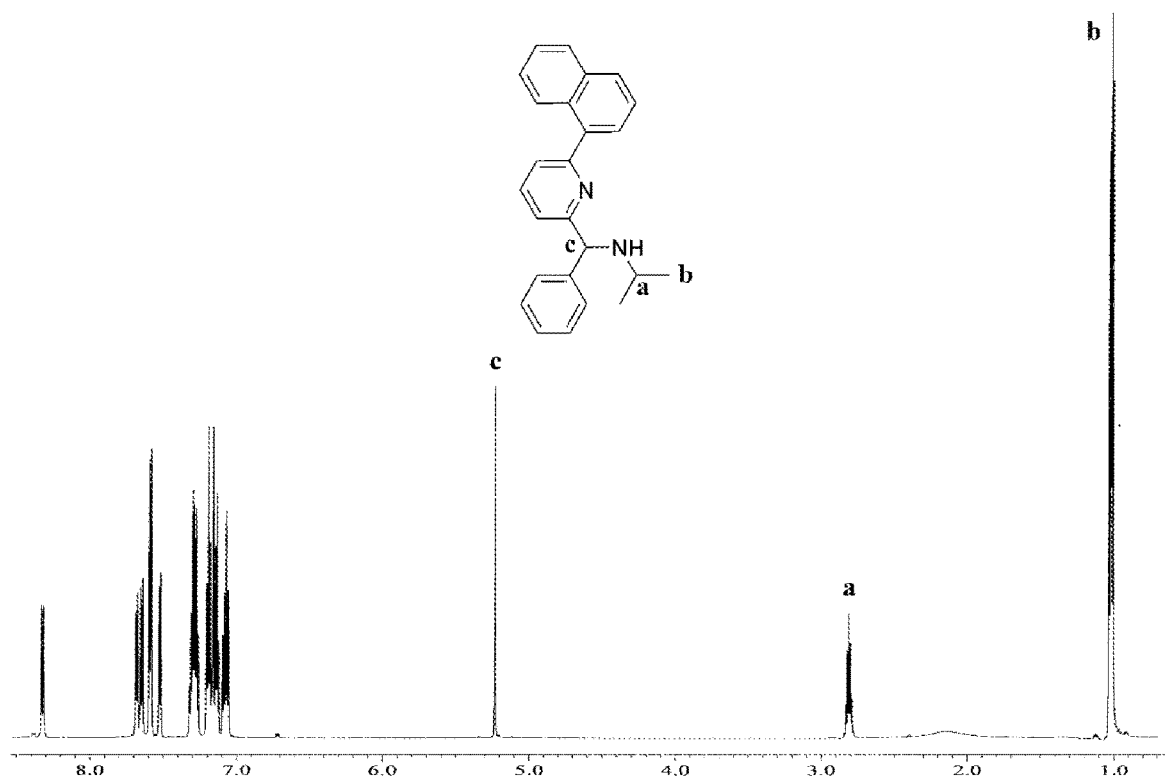
Figure 7B:
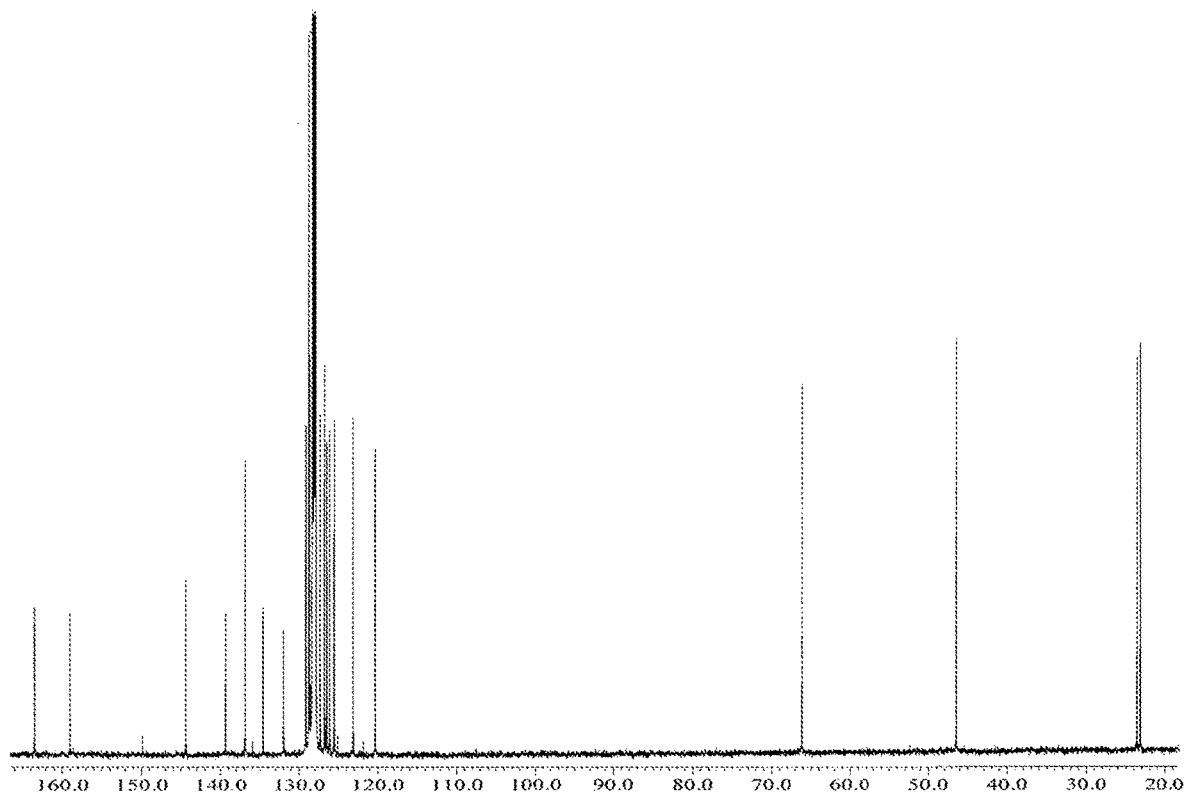

Through separating by silica gel chromatography using hexane and triethylamine (100:1 v/v), a colorless oil (0.150 g, 64%) was obtained. $^1$H and $^{13}$C NMR spectrums are shown in FIGS. 7A-B.

$^1$H NMR (600 MHz, C$_6$D$_6$): δ 8.32 (d, J=8.4 Hz, 1H), 7.68 (d, J=7.8 Hz, 1H), 7.65 (d, J=7.8 Hz, 1H), 7.59 (d, J=7.2 Hz, 2H), 7.52 (d, J=6.0 Hz, 1H), 7.34-7.24 (m, 3H), 7.24-7.11 (m, 4H), 7.11-7.04 (m, 2H), 5.23 (s, 1H, NCH), 2.81 (sept, J=6.0 Hz, 1H, CH(CH$_3$)$_2$), 0.11-0.09 (m, 6H, CH(CH$_3$)$_2$ ppm.

$^{13}$C{$^1$H} NMR (150 MHz, C$_6$D$_6$): δ 23.17, 23.57, 46.43, 66.16, 120.30, 123.12, 125.49, 126.10, 126.46, 126.77, 127.30, 127.85, 128.28, 128.63, 128.72, 129.09, 132.01, 134.58, 136.88, 139.35, 144.40, 159.02, 163.50 ppm.

IR (neat): ν 3311 (N—H) cm$^{-1}$.

HRMS (FAB): m/z calcd ([M$^+$H]+C$_{25}$H$_{24}$N$_2$) 353.2018. Found: 353.2015.

(2) Transition Metal Compound

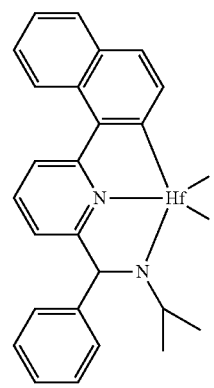

[Formula 1-3a]

Figure 8A:
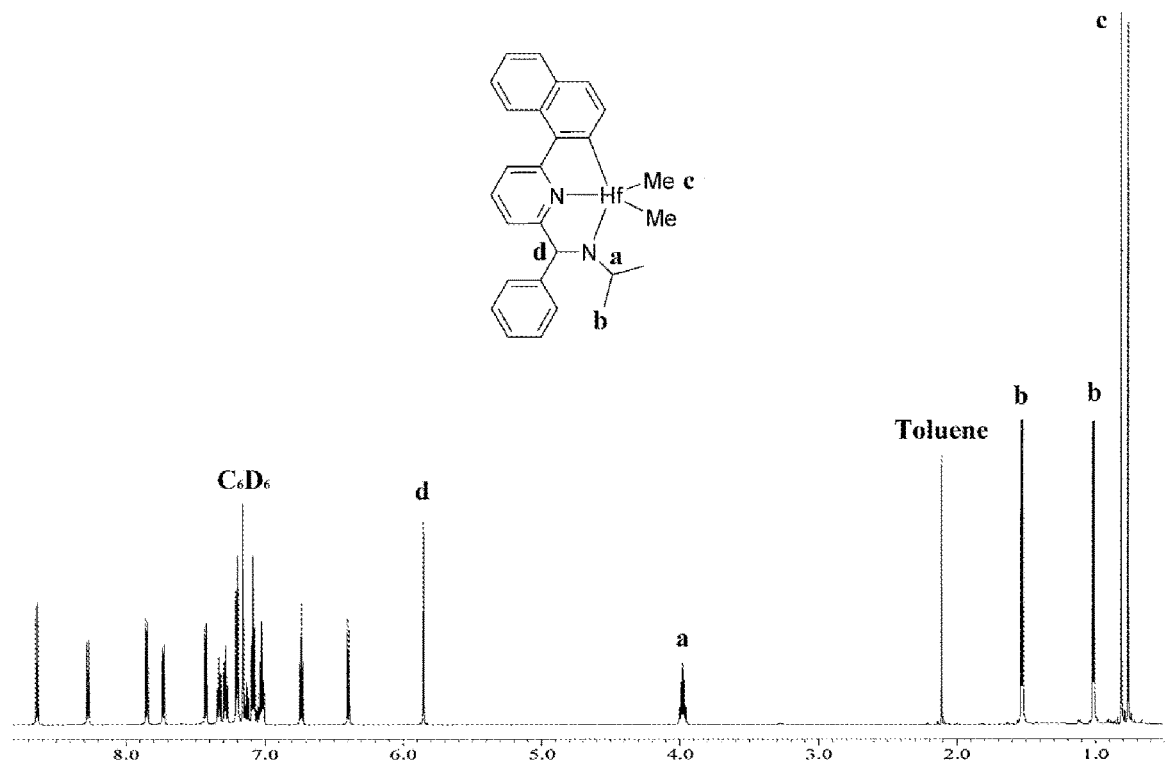
Figure 8B:
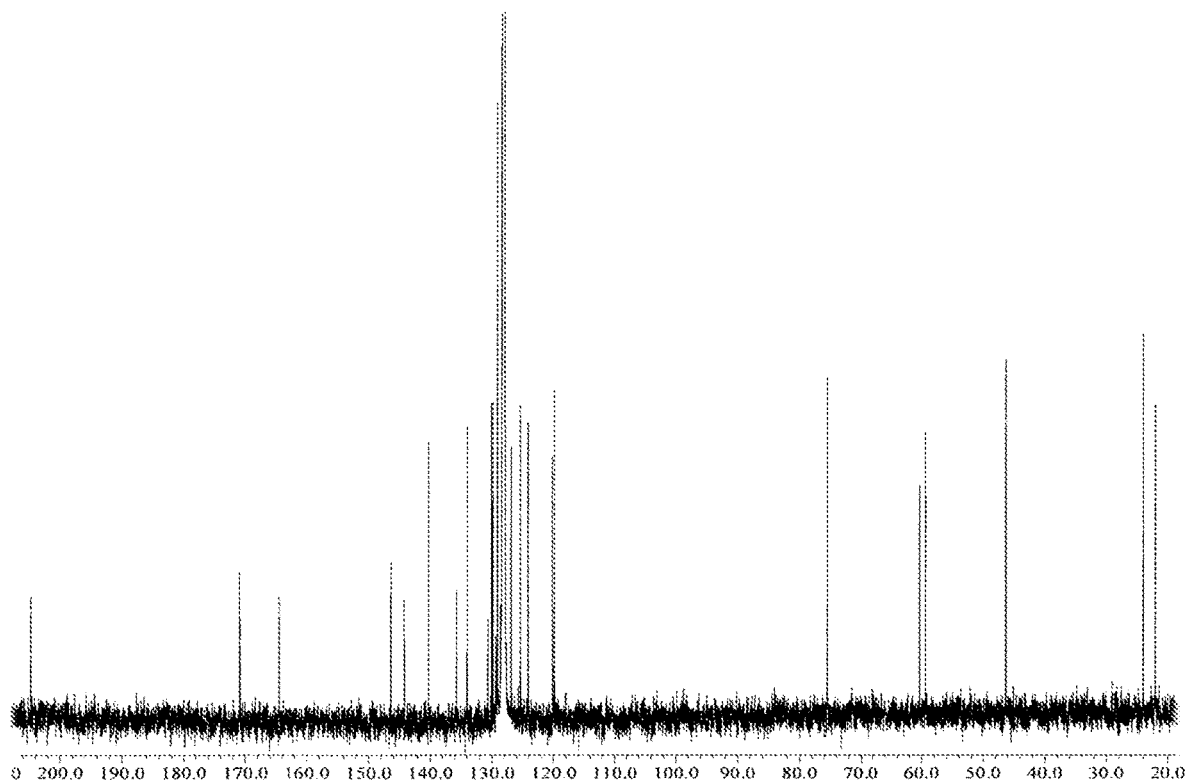

By using HfCl$_4$ (0.171 g, 0.534 mmol), MeMgBr (0.80 mL, 2.2 mmol, 3.0 M solution in diethyl ether) and the [Formula 2-3a] compound (0.126 g, 0.356 mmol) and performing the same method for preparing [Formula 1-1a], a yellow solid (0.164 g, 82%) was obtained. Through recrystallizing at −30° C. in toluene and hexane, a single crystal suitable for X-ray crystallography was obtained. $^1$H and $^{13}$C NMR spectrums are shown in FIGS. 8A-B.

$^1$H NMR (600 MHz, C$_6$D$_6$): δ 8.64 (d, J=7.2 Hz, 1H), 8.27 (d, J=8.4 Hz, 1H), 7.85 (d, J=7.2 Hz, 1H), 7.73 (d, J=8.4 Hz, 1H), 7.43 (d, J=7.2 Hz, 1H), 7.33 (t, J=7.8 Hz, 1H), 7.28 (t, J=7.2 Hz, 1H), 7.20 (d, J=7.2 Hz, 2H), 7.09 (t, J=7.2 Hz, 2H), 7.05 (t, J=7.8 Hz, 1H), 6.73 (t, J=7.8 Hz, 1H), 6.39 (d, J=7.8 Hz, 1H), 5.85 (s, 1H, NCH), 3.98 (sept, J=6.6 Hz, 1H, CH(CH$_3$)$_2$), 1.53 (d, J=3.3 Hz, 3H, CH(CH$_3$)$_2$), 1.02 (d, J=6.0 Hz, 3H, CH(CH$_3$)$_2$), 0.81 (s, 3H, HfCH$_3$), 0.77 (s, 3H, HfCH$_3$) ppm.

$^{13}$C{$^1$H} NMR (150 MHz, C$_6$D$_6$): δ 22.13, 24.04, 46.31, 59.38, 60.35, 75.52, 119.82, 120.11, 124.11, 125.35, 126.86, 129.09, 129.77, 130.01, 130.62, 133.95, 135.70, 140.23, 144.18, 146.38, 164.45, 170.90, 204.71 ppm. Anal. Calcd. (C$_{27}$H$_{28}$N$_2$Hf) C, 58.01; H, 5.05; N, 5.01%. Found: C, 58.10; H, 5.16; N, 5.09%.

Preparation Example 5: Formula 1-3b (1) Ligand Compound

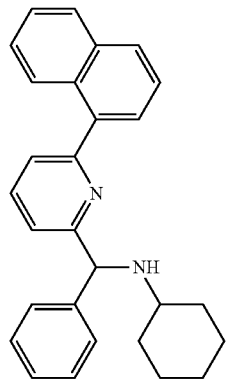

[Formula 2-3b]

The same method for preparing [Formula 2-1a] was performed using tBuLi (0.79 mL, 1.34 mmol, 1.7 M in pentane), 2-bromo-6-(naphthalene-1-yl) pyridine (0.190 g, 0.669 mmol), and PhC(H)=NCH(CH$_3$)$_3$ (0.119 g, 0.736 mmol).

Figure 9A:
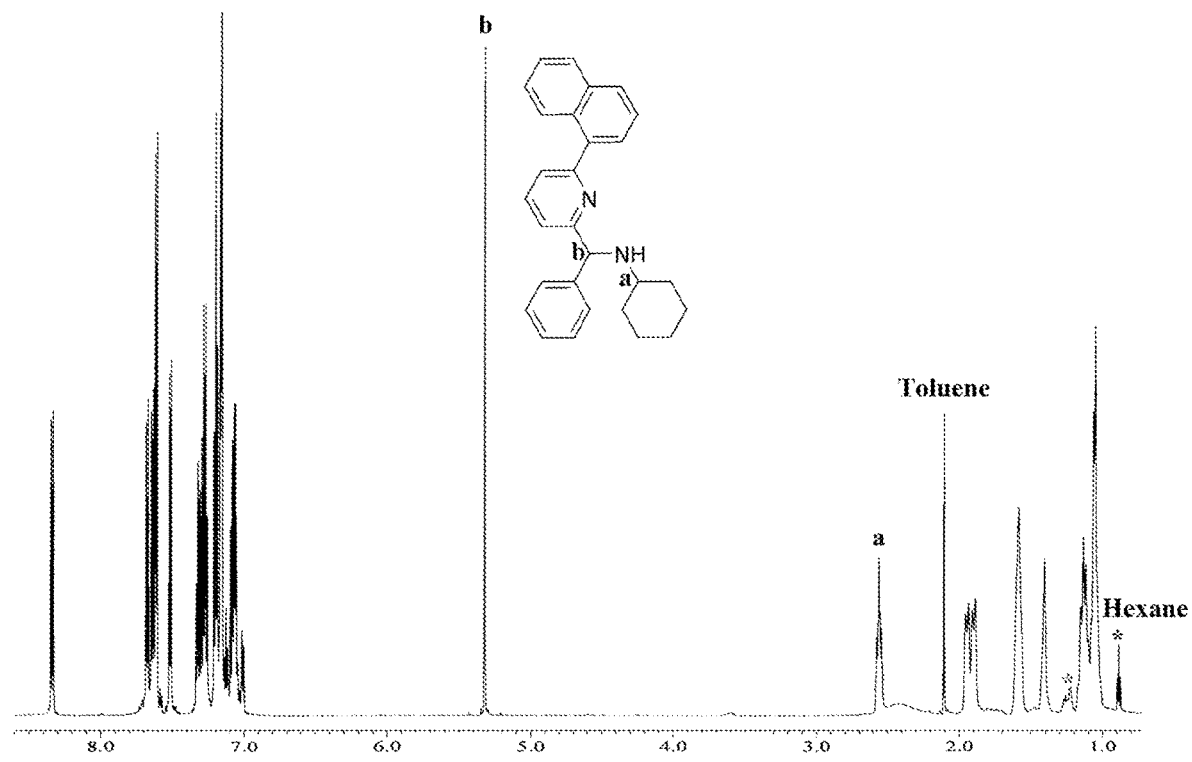
FIG. 9A shows a $^1$H NMR spectrum of the ligand compound of 2-3b.
Figure 9B:
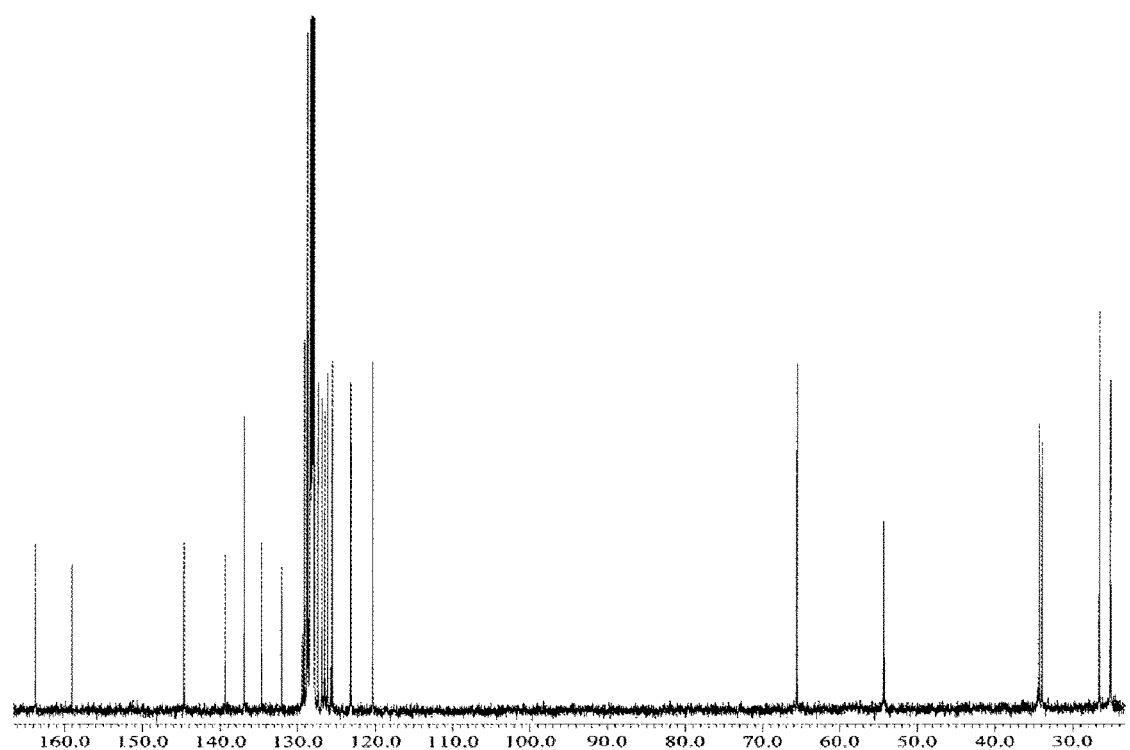
FIG. 9B shows a $^{13}$C NMR spectrum of the ligand compound of 2-3b.

Through separating by silica gel chromatography using hexane and triethylamine (100:1 v/v), a colorless oil (0.187 g, 76%) was obtained. $^1$H and $^{13}$C NMR spectrums are shown in FIGS. 9A-B.

$^1$H NMR (600 MHz, C$_6$D$_6$): δ 8.34 (d, J=8.4 Hz, 1H), 7.68 (d, J=7.2 Hz, 1H), 7.64 (d, J=7.8 Hz, 1H), 7.59 (d, J=7.8 Hz, 2H), 7.52 (d, J=7.8 Hz, 1H), 7.33-7.24 (m, 3H), 7.24-7.12 (m, 4H), 7.11-7.03 (m, 2H), 5.27 (s, 1H, NCH), 1.07 (s, 9H, C(CH$_3$)$_3$) ppm.

$^{13}$C{$^1$H} NMR (150 MHz, C$_6$D$_6$): δ 30.25, 51.64, 63.24, 120.46, 122.83, 125.49, 126.42, 126.76, 127.01, 128.69, 129.10, 132.00, 134.61, 136.79, 139.32, 146.89, 158.66, 165.02 ppm.

IR (neat): ν 3302 (N—H) cm$^{-1}$.

HRMS (EI): m/z calcd ([M$^+$] C$_{26}$H$_{26}$N$_2$) 366.2096. Found: 366.2098.

(2) Transition Metal Compound

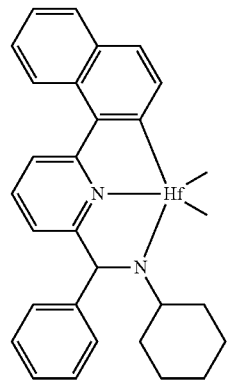

[Formula 1-3b]

Figure 10A:
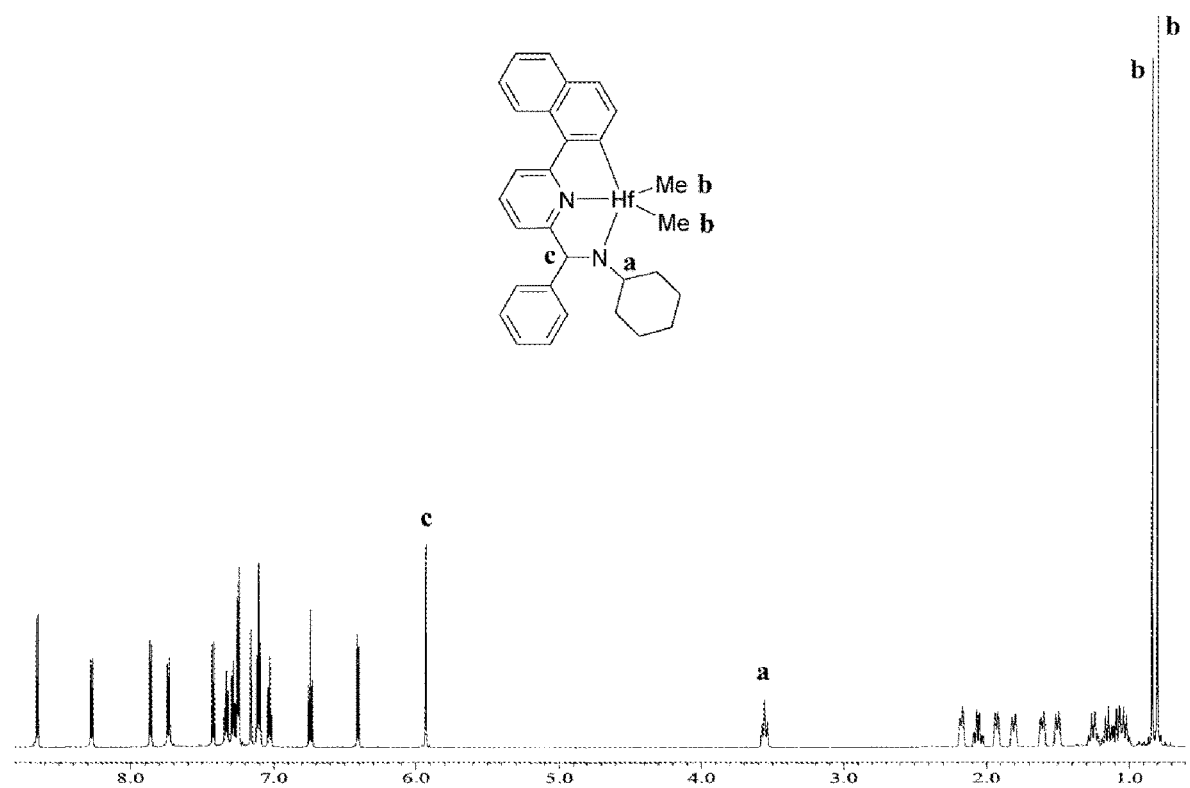
FIG. 10A shows a $^1$H NMR spectrum of the transition metal compound of 1-3b.
Figure 10B:
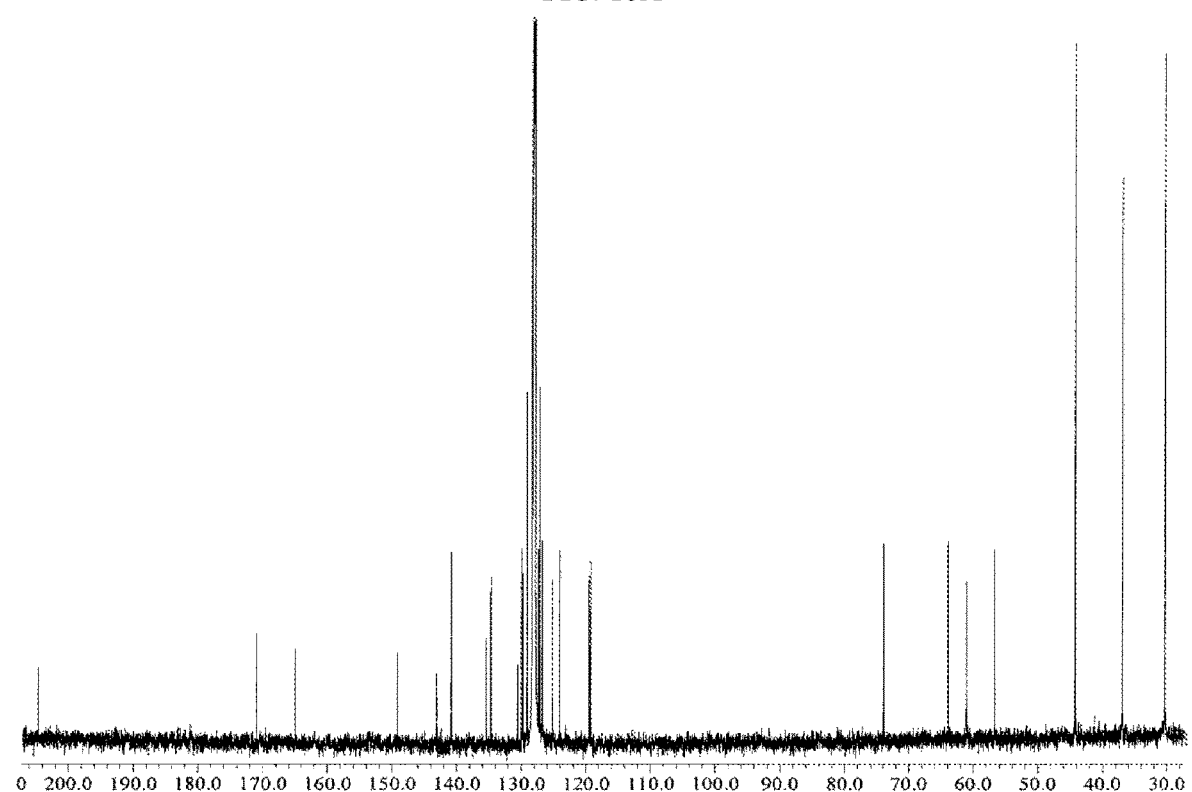
FIG. 10B shows a $^{13}$C NMR spectrum of the transition metal compound of 1-3b.

By using HfCl$_4$ (0.131 g, 0.409 mmol), MeMgBr (0.60 mL, 1.7 mmol, 3.0 M solution in diethyl ether) and the [Formula 2-3a] compound (0.100 g, 0.272 mmol) and performing the same method for preparing [Formula 1-1a], a bright brown solid (0.120 g, 79%) was obtained. $^1$H and $^{13}$C NMR spectrums are shown in FIGS. 10A-B.

$^1$H NMR (600 MHz, C$_6$D$_6$): δ 8.65 (d, J=7.2 Hz, 1H), 8.27 (d, J=8.4 Hz, 1H), 7.86 (d, J=7.8 Hz, 1H), 7.74 (d, J=8.4 Hz, 1H), 7.42 (d, J=7.8 Hz, 1H), 7.33 (t, J=7.2 Hz, 1H), 7.28 (t, J=7.2 Hz, 1H), 7.25 (d, J=7.2 Hz, 2H), 7.11 (t, J=7.2 Hz, 2H), 7.03 (t, J=7.2 Hz, 1H), 6.74 (t, J=7.2 Hz, 1H), 6.41 (d, J=8.4 Hz, 1H), 5.93 (s, 1H, NCH), 3.56 (tt, J=8.4, 3.6 Hz, 1H, C$_6$H$_{11}$), 2.17 (d, J=11.4 Hz, 1H, C$_6$H$_{11}$), 2.06 (qd, 1H, J=12, 3.6 Hz, C$_6$H$_{11}$), 1.93 (d, 1H, J=12.6 Hz, C$_6$H$_{11}$), 1.81 ((d, 1H, J=13.8 Hz, C$_6$H$_{11}$), 1.61 ((d, 1H, J=12 Hz, C$_6$H$_{11}$), 1.50 (d, 1H, J=13.2 Hz, C$_6$H$_{11}$), 1.25 (qt, 1H, J=12, 3.6 Hz, C$_6$H$_{11}$), 1.20-0.97 (m, 3H, C$_6$H$_{11}$), 0.84 (s, 3H, HfCH$_3$), 0.80 (s, 3H, HfCH$_3$) ppm.

$^{13}$C{$^1$H} NMR (150 MHz, C$_6$D$_6$): δ 26.45, 27.08, 27.49, 33.61, 35.43, 55.83, 59.25, 60.41, 75.78, 119.82, 120.10, 124.12, 125.35, 126.85, 129.08, 129.07, 130.00, 130.61, 134.00, 135.70, 140.22, 144.23, 146.53, 164.46, 170.99, 204.72 ppm. Anal. Calcd. (C$_{30}$H$_{32}$N$_2$Hf): C, 60.15; H, 5.38; N, 4.68%. Found: C, 60.32; H, 5.51; N, 4.83%.

Preparation Example 6: Formula 1-3c (1) Ligand Compound

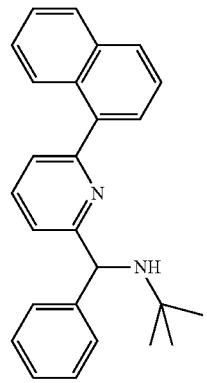

[Formula 2-3c]

The same method for preparing [Formula 2-1a] was performed using tBuLi (1.04 mL, 1.76 mmol, 1.7 M in pentane), 2-bromo-6-(naphthalene-1-yl)pyridine (0.250 g, 0.880 mmol), and PhC (H)=NC$_6$H$_{11}$ (0.181 g, 0.968 mmol).

Figure 11A:
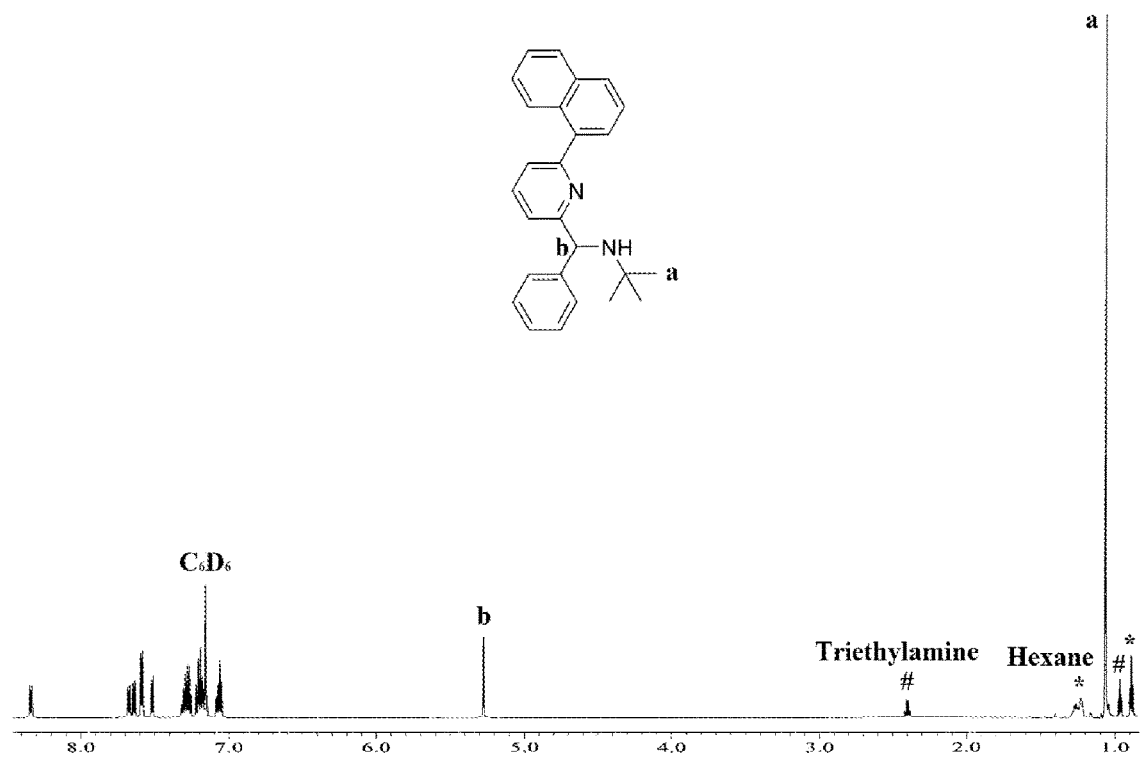
FIG. 11A shows a $^1$H NMR spectrum of the ligand compound of 2-3c.
Figure 11B:
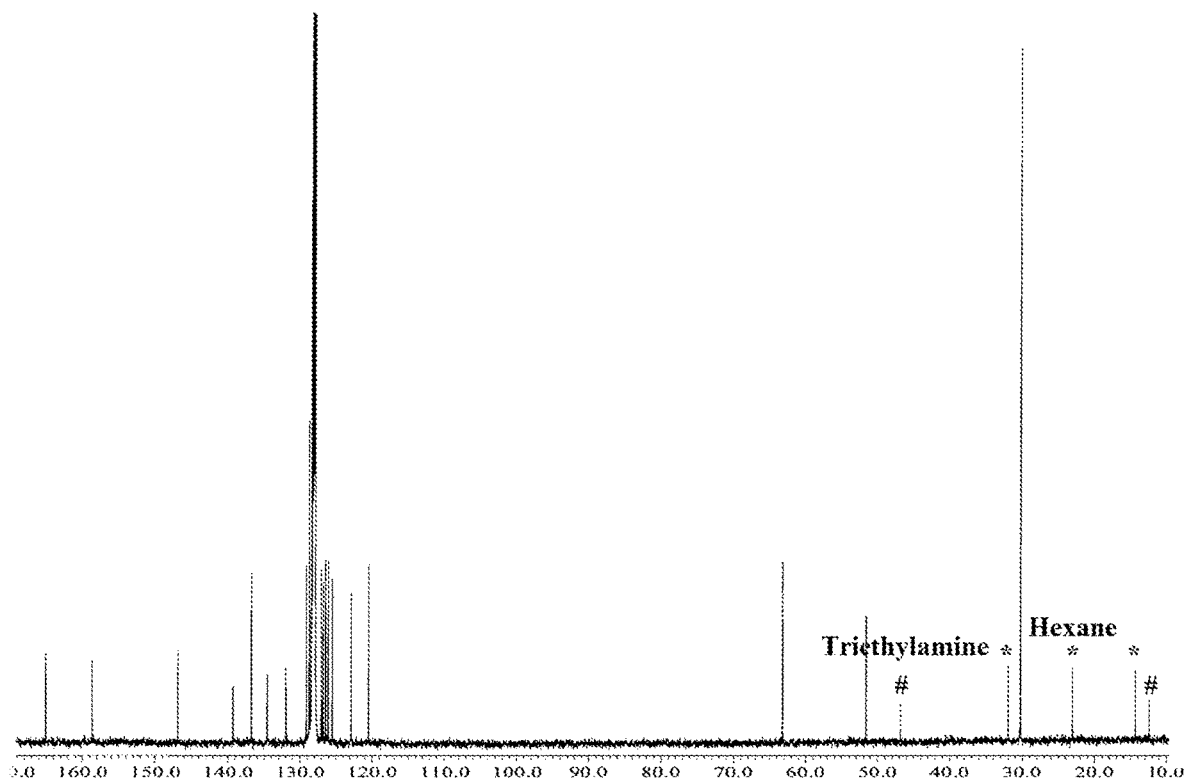
FIG. 11B shows a $^{13}$C NMR spectrum of the ligand compound of 2-3c.

Through separating by silica gel chromatography using hexane and triethylamine (100:1 v/v), a colorless oil (0.238 g, 69%) was obtained. $^1$H and $^{13}$C NMR spectrums are shown in FIGS. 11A-B.

$^1$H NMR (600 MHz, C$_6$D$_6$): δ 8.34 (d, J=7.8 Hz, 1H), 7.68 (d, J=7.2 Hz, 1H), 7.64 (d, J=8.4 Hz, 1H), 7.61 (d, J=7.2 Hz, 2H), 7.52 (d, J=6.6 Hz, 1H), 7.36-7.23 (m, 3H), 7.23-7.15 (m, 2H), 7.10-7.04 (m, 2H), 5.32 (s, 1H, NCH), 2.56 (tt, J=9.6, 3.0 Hz, 1H, C$_6$H$_{11}$), 1.94 (d, J=12 Hz, 2H, C$_6$H$_{11}$), 1.90 (d, J=12.6 Hz, 2H, C$_6$H$_{11}$), 1.59 (s, 2H, C$_6$H$_{11}$), 1.41 (s, 1H, C$_6$H$_{11}$), 1.19-0.98 (m, 5H, C$_6$H$_{11}$) ppm.

$^{13}$C{$^1$H} NMR (150 MHz, C$_6$D$_6$): δ 25.20, 26.62, 33.92, 34.29, 54.33, 65.61, 120.30, 123.12, 125.49, 126.10, 126.44, 126.80, 127.32, 128.63, 128.74, 129.10, 132.02, 134.60, 136.92, 139.36, 144.65 ppm.

IR (neat): v 3310 (N—H) cm$^{-1}$.

HRMS (FAB): m/z calcd ([M+H]$^+$ C$_{28}$H$_{28}$N$_2$) 393.2096. Found: 393.2329.

(2) Transition Metal Compound

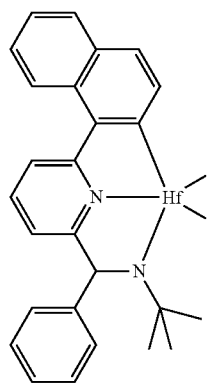

[Formula 1-3c]

Figure 12A:
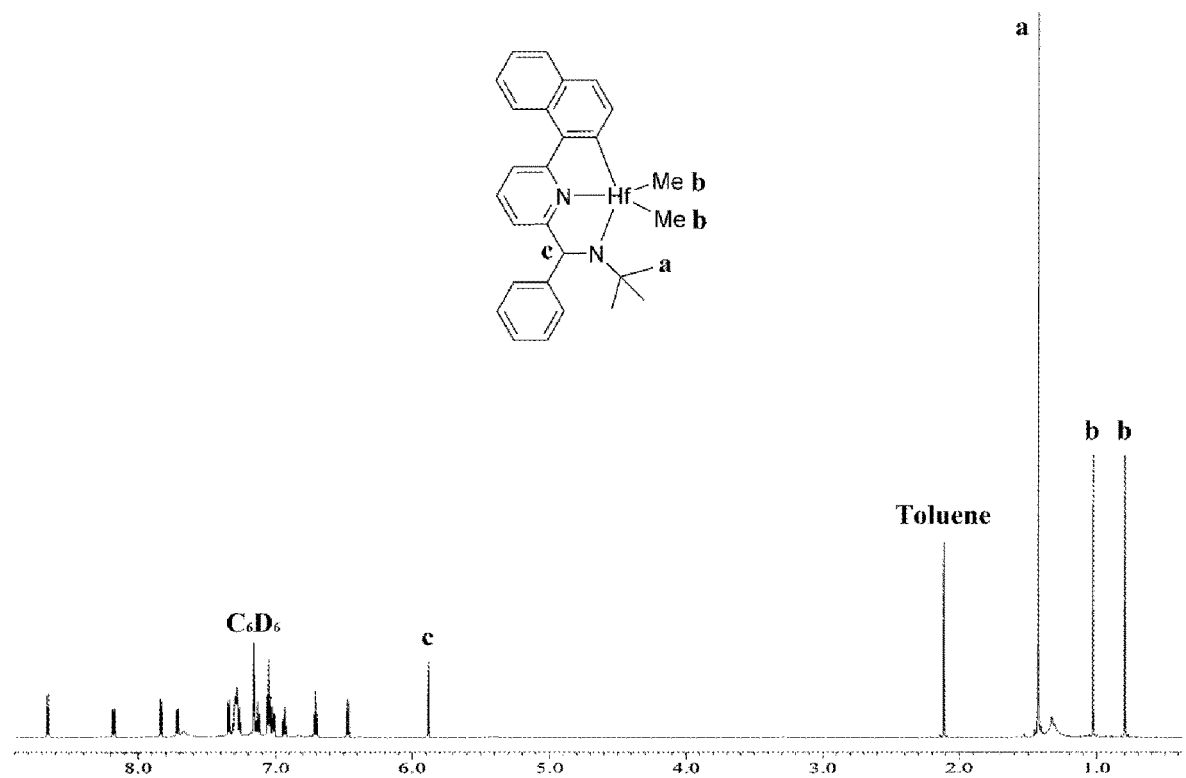
FIG. 12A shows a $^1$H NMR spectrum of the transition metal compound of 1-3c.
Figure 12B:
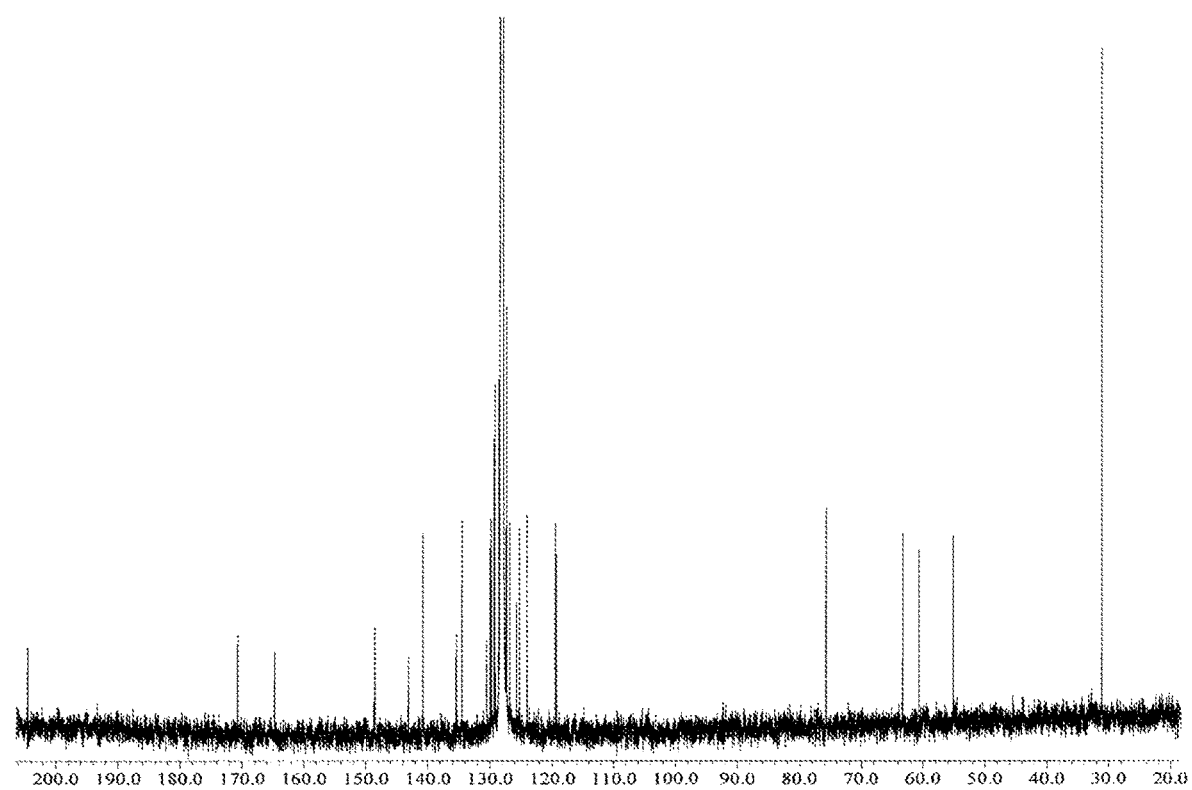
FIG. 12B shows a $^{13}$C NMR spectrum of the transition metal compound of 1-3c.

By using HfCl$_4$ (0.216 g, 0.675 mmol), MeMgBr (1.00 mL, 2.77 mmol, 3.0 M solution in diethyl ether) and the [Formula 2-3c] compound (0.165 g, 0.450 mmol) and performing the same method for preparing [Formula 1-1a], a yellow solid (0.209 g, 81%) was obtained. Through recrystallizing at −30° C. in toluene and hexane, a single crystal suitable for X-ray crystallography was obtained. $^1$H and $^{13}$C NMR spectrums are shown in FIGS. 12A-B.

$^1$H NMR (600 MHz, C$_6$D$_6$): δ 8.65 (d, J=7.8 Hz, 1H), 8.18 (d, J=8.4 Hz, 1H), 7.83 (d, J=7.2 Hz, 1H), 7.71 (d, J=7.8 Hz, 1H), 7.33-7.24 (m, 4H), 7.05 (t, J=7.2 Hz, 3H), 6.94 (t, J=7.2 Hz, 1H), 6.70 (t, J=7.2 Hz, 1H), 6.47 (d, J=7.8 Hz, 1H), 5.88 (s, 1H, NCH), 1.43 (s, 9H, C(CH$_3$)$_3$), 1.03 (s, 3H, HfCH$_3$), 0.80 (s, 3H, HfCH$_3$) ppm.

$^{13}$C{$^1$H} NMR (150 MHz, C$_6$D$_6$): δ 31.10, 55.17, 60.66, 63.223, 75.73, 119.26, 119.42, 124.02, 125.22, 126.78, 127.30, 127.42, 129.15, 129.77, 129.97, 130.55, 134.49, 135.42 ppm. Anal. Calcd. (C$_{28}$H$_{30}$N$_2$Hf): C, 58.69; H, 5.28; N, 4.89%. Found: C, 58.81; H, 5.38; N, 4.97%.

Preparation Example 7: Formula 1-3d (1) Ligand Compound

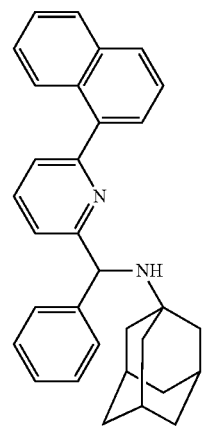

[Formula 2-3d]

The same method for preparing [Formula 2-1a] was performed using tBuLi (1.04 mL, 1.76 mmol, 1.7 M in pentane), 2-bromo-6-(naphthalene-1-yl)pyridine (0.250 g, 0.880 mmol), and PhC (H)=NC$_{10}$H$_{16}$ (0.232 g, 0.968 mmol).

Figure 13A:
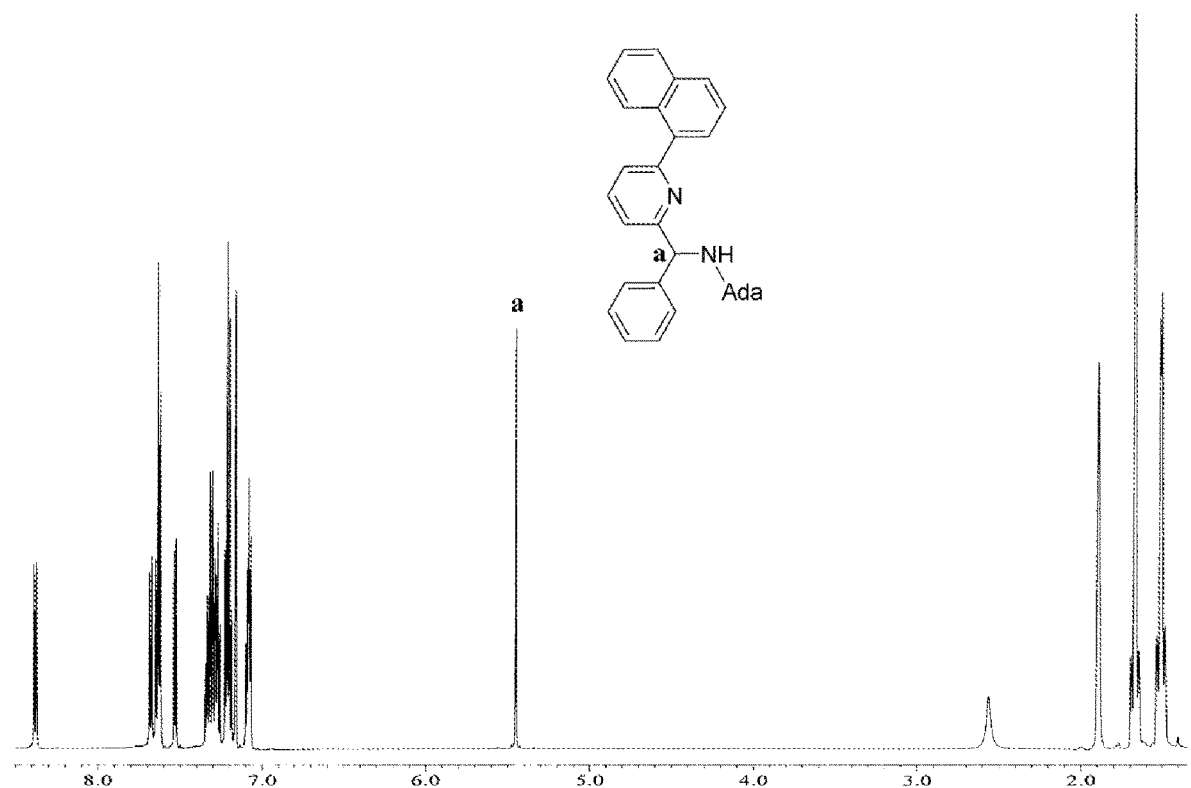
FIG. 13A shows a $^1$H NMR spectrum of the ligand compound of 2-3d.
Figure 13B:
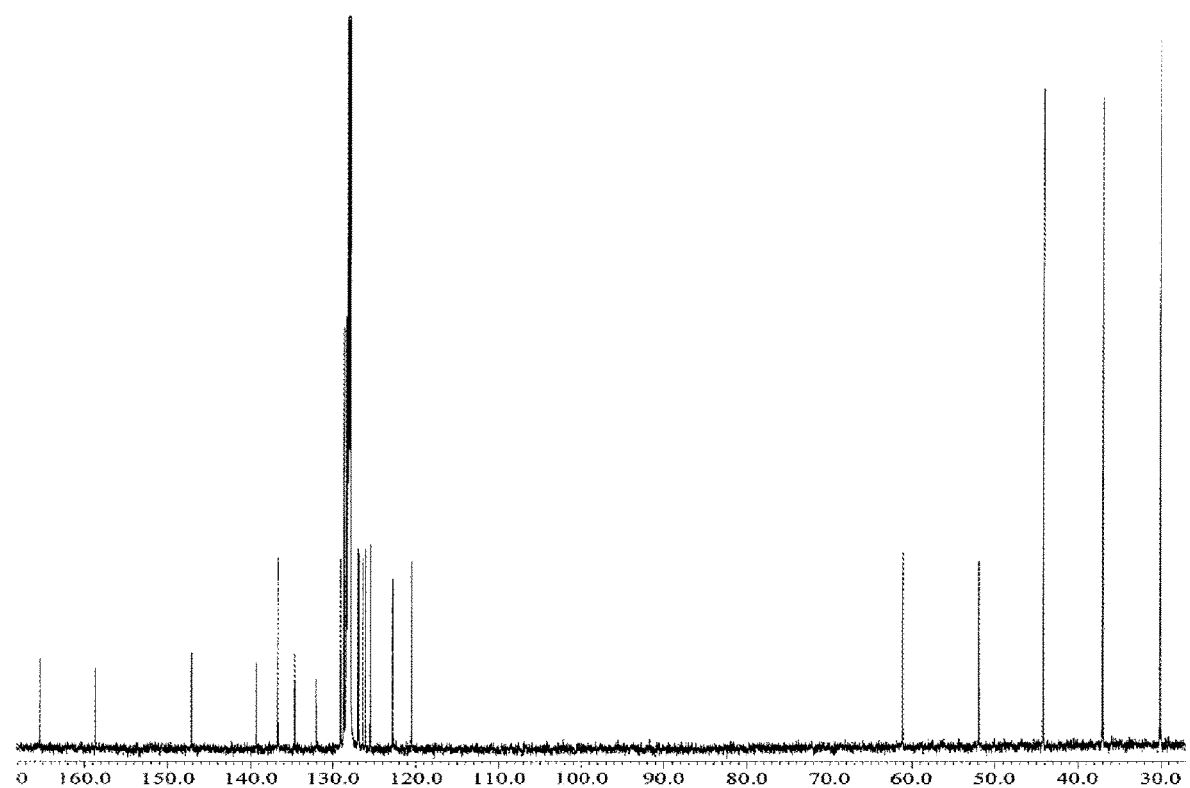
FIG. 13B shows and a $^{13}$C NMR spectrum of the ligand compound of 2-3d.

Through separating by silica gel chromatography using hexane and triethylamine (100:1 v/v), a white glassy solid (0.260 g, 74%) was obtained. $^1$H and $^{13}$C NMR spectrums are shown in FIGS. 13A-B.

$^1$H NMR (600 MHz, C$_6$D$_6$): δ 8.38 (d, J=7.8 Hz, 1H), 7.68 (d, J=8.4 Hz, 1H), 7.66-7.59 (m, 4H), 7.53 (d, J=7.2 Hz, 2H), 7.37-7.25 (m, 4H), 7.25-7.18 (m, 3H), 7.12-7.05 (m, 2H), 5.45 (s, 1H, NCH), 2.56 (s, 1H, C$_{10}$H$_{16}$), 1.90 (s, 3H, C$_{10}$H$_{16}$), 1.67 (t, 6H, J=15 Hz, C$_{10}$H$_{16}$), 1.51 (dd, 6H, J=19.8, 12 Hz, C$_{10}$H$_{16}$) ppm.

$^{13}$C{$^1$H} NMR (150 MHz, C$_6$D$_6$): δ 30.15, 37.03, 44.20, 51.93, 61.16, 120.49, 122.80, 125.49, 126.08, 126.40, 126.87, 126.97, 127.98, 128.39, 128.63, 128.67, 129.10, 132.02, 134.63, 136.79, 139.35 ppm.

IR (neat): v 3293 (N—H) cm$^{-1}$.

HRMS (EI): m/z calcd ([M$^+$] C$_{32}$H$_{32}$N$_2$) 444.2565. Found: 444.2563.

(2) Transition Metal Compound

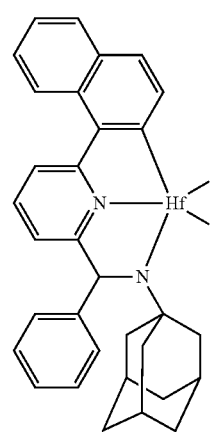

[Formula 1-3d]

Figure 14A:
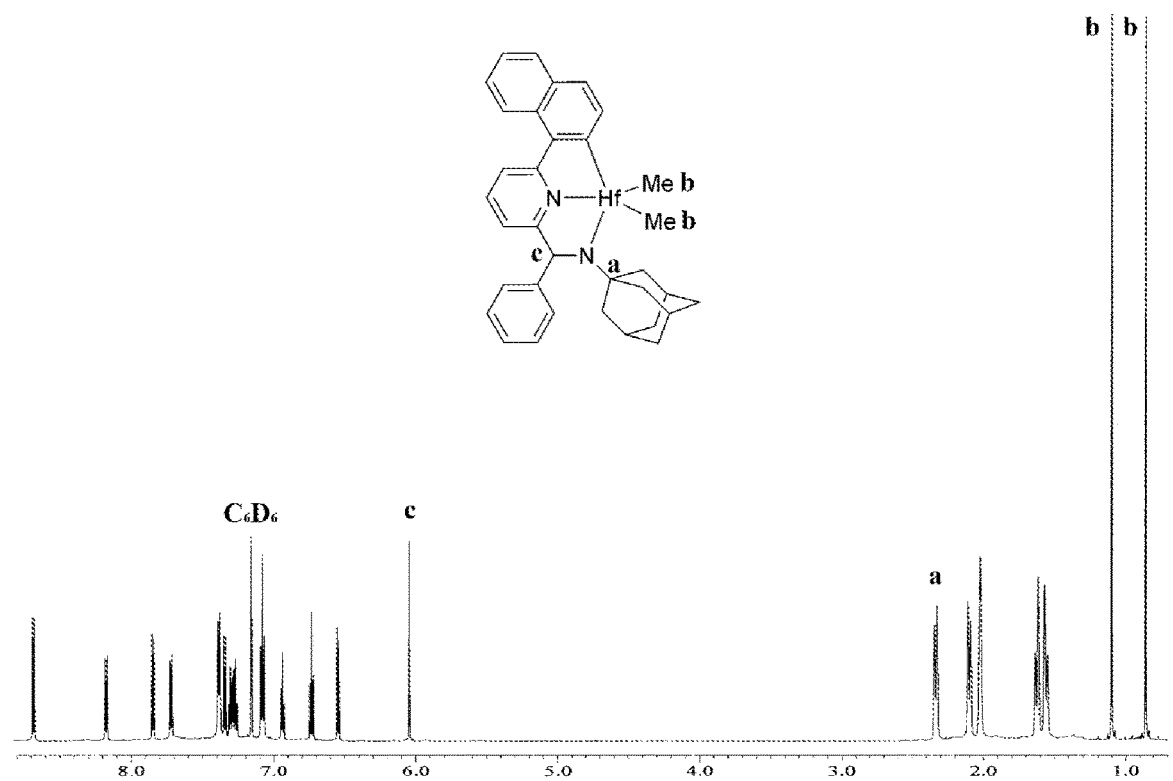
FIG. 14A shows a $^1$H NMR spectrum of the transition metal compound of 1-3d.
Figure 14B:
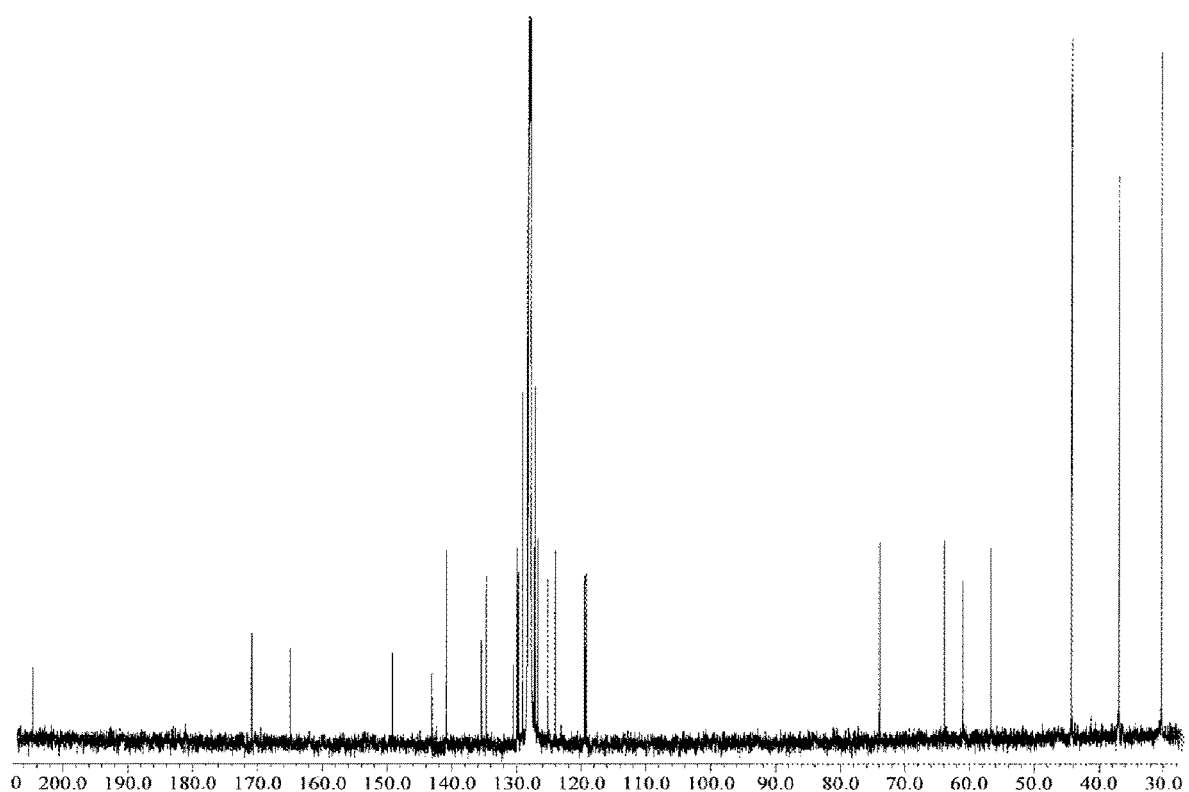
FIG. 14B shows a $^{13}$C NMR spectrum of the transition metal compound of 1-3d.

By using HfCl$_4$ (0.256 g, 0.800 mmol), MeMgBr (1.10 mL, 3.28 mmol, 3.0 M solution in diethyl ether) and the [Formula 2-3d] compound (0.237 g, 0.533 mmol) and performing the same method for preparing [Formula 1-1a], a yellow solid (0.288 g, 83%) was obtained. Through recrystallizing at −30° C. in a toluene/hexane cosolvent, a single crystal suitable for X-ray crystallography was obtained. $^1$H and $^{13}$C NMR spectrums are shown in FIGS. 14A-B.

$^1$H NMR (600 MHz, C$_6$D$_6$): δ 8.68 (d, J=7.8 Hz, 1H), 8.17 (d, J=8.4 Hz, 1H), 7.85 (d, J=7.8 Hz, 1H), 7.72 (d, J=8.4 Hz, 1H), 7.38 (d, J=8.4 Hz, 2H), 7.34 (d, J=8.4 Hz, 1H), 7.33-7.25 (m, 2H), 7.08 (t, J=7.8 Hz, 2H), 6.94 (t, J=7.8 Hz, 1H), 6.73 (t, J=7.8 Hz, 1H), 6.54 (d, J=7.8 Hz, 1H), 6.05 (s, 1H, NCH), 2.33 (d, 3H, J=11.4 Hz, C$_{10}$H$_{16}$), 2.10 (d, 3H, J=10.8 Hz, C$_{10}$H$_{16}$), 2.02 (s, 3H, C$_{10}$H$_{16}$), 1.62 (d, 3H, J=12 Hz, C$_{10}$H$_{16}$), 1.56 (d, 3H, J=11.4 Hz, C$_{10}$H$_{16}$), 1.10 (s, 3H, HfCH$_3$), 0.86 (s, 3H, HfCH$_3$) ppm.

$^{13}$C{$^1$H} NMR (150 MHz, C$_6$D$_6$): δ 30.30, 36.98, 44.25, 56.72, 61.04, 63.92, 73.91, 119.18, 119.44, 124.04, 125.20, 126.76, 127.16, 127.35, 127.98, 129.11, 129.73, 129.95, 130.55, 134.67, 135.42, 140.80, 143.10, 149.16, 164.91, 170.90, 204.57 ppm. Anal. Calcd. (C$_{34}$H$_{36}$N$_2$Hf): C, 62.71; H, 5.57; N, 4.30%. Found: C, 62.59; H, 5.44; N, 4.18%.

Comparative Preparation Example 1

(1) Ligand Compound

The same method for preparing [Formula 2-1a] was performed using tBuLi (0.79 mL, 1.34 mmol, 1.7 M in pentane), 2-bromo-6-(naphthalene-1-yl) pyridine (0.190 g, 0.669 mmol), and (Z)—N-(2-isopropylbenzylidene)aniline (0.165 g, 0.740 mmol).

The same method for preparing [Formula 1-1a] was performed using HfCl$_4$ (0.256 g, 0.800 mmol), MeMgBr (1.10 mL, 3.28 mmol, 3.0 M solution in diethyl ether), and the ligand compound (0.237 g, 0.533 mmol).

(2) Transition Metal Compound

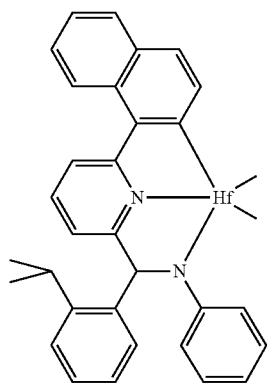

The same method for preparing [Formula 1-1a] was performed using HfCl$_4$ (0.256 g, 0.800 mmol), MeMgBr (1.10 mL, 3.28 mmol, 3.0 M solution in diethyl ether), and the ligand compound (0.237 g, 0.533 mmol).

Comparative Preparation Example 2

(1) Ligand Compound

The method disclosed in a document [Organometallics 2011, 30, 6028-6033] was performed.

(2) Transition Metal Compound

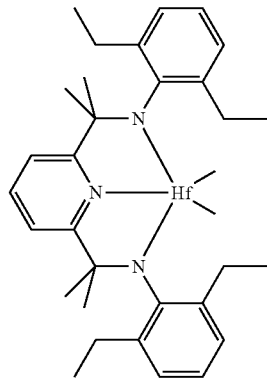

The same method for preparing [Formula 1-1a] was performed using HfCl$_4$ (0.158 g, 0.492 mmol), MeMgBr (0.700 mL, 2.08 mmol, 3.0 M solution in diethyl ether), the ligand compound (0.150 g, 0.328 mmol) and toluene (6 mL).

Comparative Preparation Example 3

(1) Ligand Compound

A Schlenk flask was charged under N$_2$ atmosphere with (5-bromothiophene-2-yl)-N-(2,6-diisopropylphenyl)methaneimine (1.00 g, 2.86 mmol), 1-naphthylboronic acid (0.491 g, 2.86 mmol), Na$_2$CO$_3$ (0.759 g, 7.17 mmol) and toluene (3 mL). A solution of (Ph$_3$P)$_4$Pd (9.0 mg, 0.0080 mmol) in degassed H$_2$O/EtOH (2 mL, 1:1 v/v) and toluene (1 mL) was added thereto. The two-phase solution thus obtained was heated to 70° C. and vigorously stirred overnight. After cooling to room temperature, organic phases were collected and washed with H$_2$O (5 mL). The collected organic phase was dried on an anhydrous MgSO$_4$ phase, and solvents were removed by a rotary evaporator. Through separating by recrystallizing in methanol at −30° C., (E)-N-((5-(naphthalane-1-yl)thiophene-2-yl)methylene)aniline was obtained as a yellow solid (0.738 g, 65%).

nBuLi (0.90 mL, 1.4 mmol, 1.61 M solution in hexane) was dropwisely added to a solution of (E)-N-((5-(naphthalene-1-yl)thiophene-2-yl)methylene)aniline (0.500 g, 1.26 mmol) in toluene (10 mL). After stirring for 1 hours, water (10 mL) was added, and the resultant product was extracted with toluene (3×5 mL). A mixed organic phase was dried on an anhydrous MgSO$_4$ phase, and solvents were removed by a rotary evaporator. Through the analysis by $^1$H and $^{13}$C NMR spectrums, the crude oil thus obtained was confirmed pure and was used in a subsequent step without additional separation (0.573 g, 100%).

(2) Transition Metal Compound

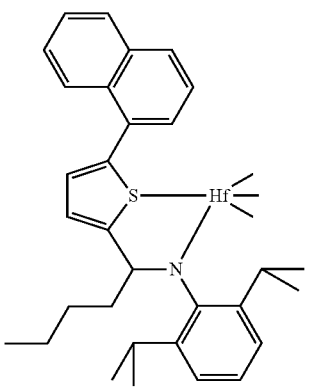

The same method for preparing [Formula 1-1a] was performed using HfCl$_4$ (0.229 g, 0.716 mmol), MeMgBr (1.00 mL, 2.94 mmol, 3.0 M solution in diethyl ether), and the ligand compound (0.251 g, 0.551 mmol).

Preparation of Olefin Polymers

Example 1

A bomb reactor (125 mL) was vacuum treated at 60° C. for 1 hour. After charging the bomb reactor with an ethylene gas of an atmospheric pressure, a solution of Me$_3$Al (28.8 mg, 200 μmol-Al) in methylcyclohexane (15.5 g) was added to the reactor. The mixture thus obtained was stirred at 100° C. for 1 hour using a mantle, and then, a solution was removed using a cannular. The reactor was emptied out again to remove remaining solvents, and recharged with an ethylene gas under an atmospheric pressure. This procedure was performed for purge catalyst poison.

The reactor was charged with methylcyclohexane (15.5 g) containing MMAO (AkzoNobel, 6.7 wt %-Al in heptane, 20 mg, 50 μmol-Al), and the temperature was set to 80° C. The transition metal compound of Preparation Example 1 was reacted with a cocatalyst [(C$_{18}$H$_{37}$)$_2$N(H)Me]$^+$[B(C$_6$F$_5$)$_4$]$^-$ (1.0 eq) for activation, and a methylcyclohexane solution (0.30 g) containing an activated catalyst (2.0 μmol-Hf) was injected.

The reactor was charged with an ethylene/propylene mixture gas (15 bar/15 bar, total 30 bar) at 30 bar from a tank, and polymerization was performed at 80-90° C. for 50 minutes. The ethylene/propylene mixture gas was exhausted, and the reactor was cooled to 75° C. The polymer thus produced was collected and dried in a vacuum oven of 160° C. overnight.

Examples 2 to 7, and Comparative Examples 1 to 3

Olefin polymers were prepared by the same method as in Example 1 except for changing the type of the catalyst as in Table 1 below.

TABLE 1

| | Catalyst |
|---|---|
| Example 1 | Preparation Example 1 |
| Example 2 | Preparation Example 2 |
| Example 3 | Preparation Example 3 |

TABLE 1-continued

| | Catalyst |
|---|---|
| Example 4 | Preparation Example 4 |
| Example 5 | Preparation Example 5 |
| Example 6 | Preparation Example 6 |
| Example 7 | Preparation Example 7 |
| Comparative Example 1 | Comparative Preparation Example 1 |
| Comparative Example 2 | Comparative Preparation Example 2 |
| Comparative Example 3 | Comparative Preparation Example 3 |

Experimental Example 1

The polymerization results of the olefin polymer were analyzed by the methods below.

(1) Melting Temperature (Tm, ° C.)

The melting temperature of a polymer was measured using a differential scanning calorimeter (DSC, apparatus name: DSC 2920, manufacturer: TA instrument). Particularly, a polymer was heated to 150° C., this temperature was kept for 5 minutes, the temperature was decreased to −100° C., and the temperature was increased again. In this case, the increasing rate and decreasing rate of the temperature were controlled to 10° C./min, respectively. The melting temperature was set to the maximum point of an absorption peak measured in the second increasing section of the temperature.

(2) Number Average Molecular Weight (Mn) and Molecular Weight Distribution (MWD)

After pretreating by dissolving in 1,2,4-trichlorobenzene containing 0.0125% of BHT at 160° C. for 3 hours using PL-SP260, the weight average molecular weight (Mw) and the number average molecular weight (Mn) were respectively measured at a measurement temperature of 160° C. using PL-GPC220. In this case, each molecular weight was measured by standardizing using polystyrene. By using Mw and Mn thus measured, MWD was calculated by dividing a Mw value by a Mn value.

TABLE 2

| | Catalyst | Yield (g) | [C$_3$H$_6$] (mol %) | T$_m$ | M$_n$ (kDa) | MWD (M$_w$/M$_n$) |
|---|---|---|---|---|---|---|
| Example 1 | Preparation Example 1 | 0.9 | 2.4 | 111-122 | 45 | 2.0 |
| Example 2 | Preparation Example 2 | 0.8 | 2.3 | 112-123 | 43 | 2.2 |
| Example 3 | Preparation Example 3 | 1.4 | 2.1 | 114-123 | 450 | 2.3 |
| Example 4 | Preparation Example 4 | 1.2 | 2.9 | 108-118 | 30 | 1.8 |
| Example 5 | Preparation Example 5 | 1.5 | 3.1 | 106-116 | 31 | 1.7 |
| Example 6 | Preparation Example 6 | 1.9 | 3.2 | 103-115 | 42 | 1.7 |
| Example 7 | Preparation Example 7 | 2.1 | 5.2 | 90-109 | 55 | 1.6 |
| Comparative Example 1 | Comparative Preparation Example 1 | 0.4 | 1.8 | 115-125 | 10 | 3.3 |
| Comparative Example 2 | Comparative Preparation Example 2 | — | — | — | — | — |
| Comparative Example 3 | Comparative Preparation Example 3 | — | — | — | — | — |

As shown in Table 2 above, the compound according to the present invention was useful as a catalyst in the copolymerization reaction of ethylene and propylene, and an ethylene/propylene copolymer could be successfully obtained.

On the contrary, the compounds of Comparative Preparation Example 2 and Comparative Preparation Example 3 did not show activity as a catalyst, and polymerization reaction was not properly performed, and an ethylene/propylene copolymer was obtained little.

In addition, Comparative Example 1 used the compound of Comparative Preparation Example 1 in which X was an aryl group of 6 to 20 carbon atoms, and the aryl group was positioned at $R_6$, different from the compound of the present invention, and it was confirmed that the yield and the mixing capacity of alpha-olefin were markedly decreased when compared with the compound of Preparation Example 7, and a copolymer having a high number average molecular weight could not be prepared.

The invention claimed is:

1. A transition metal compound represented by the following Formula 1:

[Formula 1]

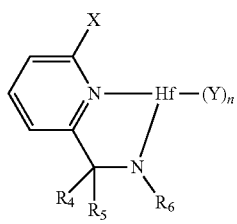

in Formula 1,

X is —Si($R_1$)($R_2$)($R_3$), or an aryl group of 6 to 20 carbon atoms, where any one among $R_1$ to $R_3$ or the aryl group of 6 to 20 carbon atoms is optionally combined with Hf to form a five-member ring, $R_1$ to $R_3$ are each independently an alkyl group of 1 to 20 carbon atoms, a cycloalkyl group of 3 to 20 carbon atoms, an aryl group of 6 to 20 carbon atoms, an alkylaryl group of 7 to 20 carbon atoms, or an arylalkyl group of 7 to 20 carbon atoms, $R_4$ and $R_5$ are each independently hydrogen, an alkyl group of 1 to 20 carbon atoms, an alkenyl group of 2 to 20 carbon atoms, an alkynyl group of 2 to 20 carbon atoms, a cycloalkyl group of 3 to 20 carbon atoms, an aryl group of 6 to 20 carbon atoms, an alkylaryl group of 7 to 20 carbon atoms, or an arylalkyl group of 7 to 20 carbon atoms, $R_6$ is hydrogen, an alkyl group of 1 to 20 carbon atoms, a cycloalkyl group of 3 to 20 carbon atoms, an aryl group of 6 to 20 carbon atoms, an alkylaryl group of 7 to 20 carbon atoms, or an arylalkyl group of 7 to 20 carbon atoms, where if X is an aryl group of 6 to 20 carbon atoms, $R_6$ is hydrogen, a branched alkyl group of 3 to 20 carbon atoms, or an unsubstituted cycloalkyl group of 3 to 20 carbon atoms, each Y is independently halogen, an alkyl group of 1 to 20 carbon atoms, an alkenyl group of 2 to 20 carbon atoms, an alkynyl group of 2 to 20 carbon atoms, a cycloalkyl group of 3 to 20 carbon atoms, an aryl group of 6 to 20 carbon atoms, an alkylaryl group of 7 to 20 carbon atoms, an arylalkyl group of 7 to 20 carbon atoms, a heteroaryl group of 5 to 20 carbon atoms, an alkoxy group of 1 to 20 carbon atoms, a substituted or unsubstituted aryloxy group of 5 to 20 carbon atoms, an alkylamino group of 1 to 20 carbon atoms, an arylamino group of 5 to 20 carbon atoms, an alkylthio group of 1 to 20 carbon atoms, an arylthio group of 5 to 20 carbon atoms, an alkylsilyl group of 1 to 20 carbon atoms, an arylsilyl group of 5 to 20 carbon atoms, a hydroxyl group, an amino group, a thio group, a silyl group, a cyano group, or a nitro group, and n is an integer of 2 to 4.

2. The transition metal compound according to claim 1, wherein $R_1$ to $R_3$ are each independently an alkyl group of 1 to 20 carbon atoms, or an aryl group of 6 to 20 carbon atoms, $R_4$ and $R_5$ are each independently hydrogen, an alkyl group of 1 to 20 carbon atoms, or an aryl group of 6 to 20 carbon atoms, $R_6$ is an alkyl group of 1 to 20 carbon atoms, a substituted or unsubstituted cycloalkyl group of 3 to 20 carbon atoms, or a substituted or unsubstituted aryl group of 6 to 20 carbon atoms, each Y is independently an alkyl group of 1 to 20 carbon atoms, a substituted or unsubstituted cycloalkyl group of 3 to 20 carbon atoms, or a substituted or unsubstituted aryl group of 6 to 20 carbon atoms, and n is 2 or 3.

3. The transition metal compound according to claim 1, which is represented by Formulae 1-1, 1-2 or 1-3:

[Formula 1-1]

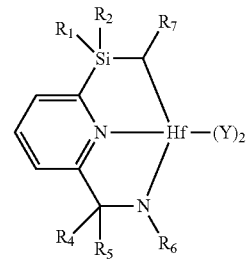

[Formula 1-2]

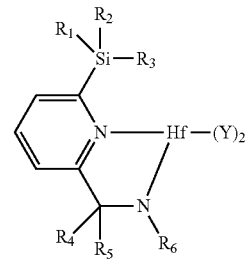

[Formula 1-3]

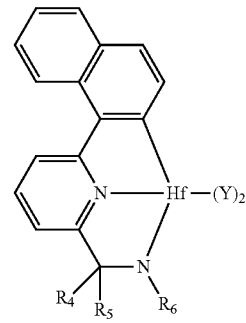

in Formulae 1-1 to 1-3, $R_1$ to $R_6$ is the same as in Formula 1, and $R_7$ is an alkyl group of 1 to 19 carbon atoms, an aryl group of 6 to 19 carbon atoms, or an arylalkyl group of 7 to 19 carbon atoms.

4. The transition metal compound according to claim 1, which is represented by Formulae 1-1a, 1-1b, 1-2a, 1-3a, 1-3b, 1-3c or 1-3d:

[Formula 1-1a]
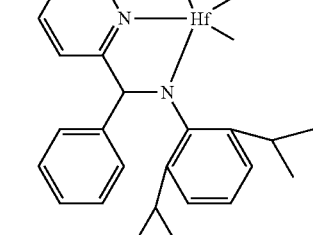
[Formula 1-1b]
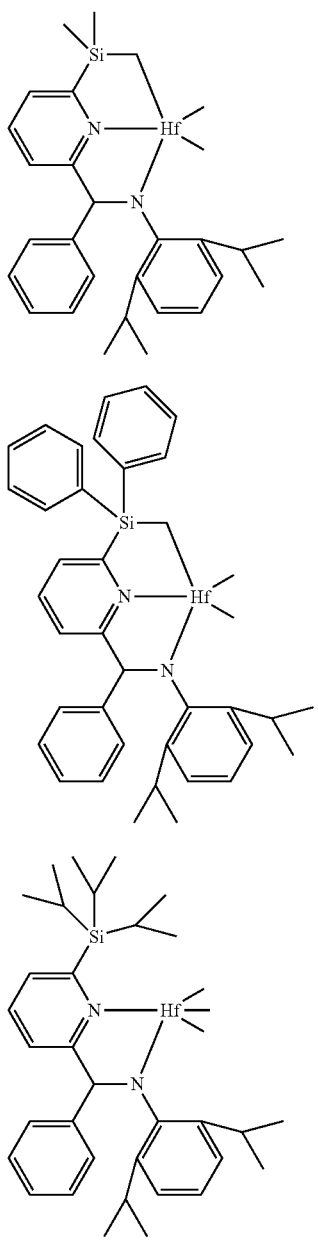
[Formula 1-2a]
[Formula 1-3a]
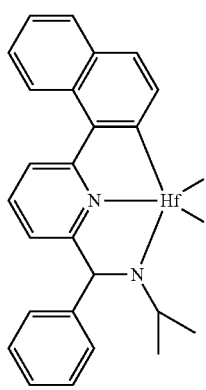
[Formula 1-3b]
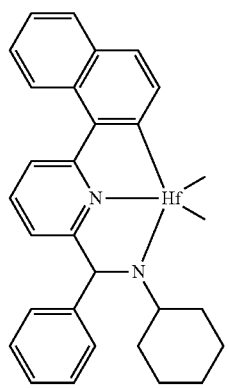
[Formula 1-3c]
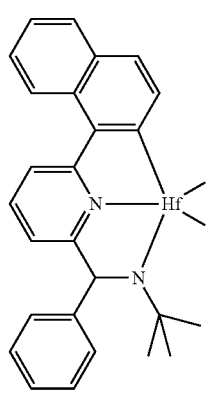
[Formula 1-3d]
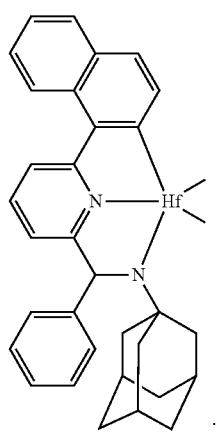
5. A ligand compound represented by the following Formula 2:
[Formula 2]
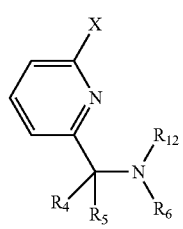
in Formula 2,
X is $-Si(R_1)(R_2)(R_3)$, or an aryl group of 6 to 20 carbon atoms, R₁ to R₃ are each independently an alkyl group of 1 to 20 carbon atoms, a cycloalkyl group of 3 to 20 carbon atoms, an aryl group of 6 to 20 carbon atoms, an alkylaryl group of 7 to 20 carbon atoms, or an arylalkyl group of 7 to 20 carbon atoms, R₄ and R₅ are each independently hydrogen, an alkyl group of 1 to 20 carbon atoms, an alkenyl group of 2 to 20 carbon atoms, an alkynyl group of 2 to 20 carbon atoms, a cycloalkyl group of 3 to 20 carbon atoms, an aryl group of 6 to 20 carbon atoms, an alkylaryl group of 7 to 20 carbon atoms, or an arylalkyl group of 7 to 20 carbon atoms, R₆ is hydrogen, an alkyl group of 1 to 20 carbon atoms, a cycloalkyl group of 3 to 20 carbon atoms, an aryl group of 6 to 20 carbon atoms, an alkylaryl group of 7 to 20 carbon atoms, or an arylalkyl group of 7 to 20 carbon atoms, where if X is an aryl group of 6 to 20 carbon atoms, R₆ is hydrogen, a branched alkyl group of 6 to 20 carbon atoms, or an unsubstituted cycloalkyl group of 3 to 20 carbon atoms, and R₁₂ is hydrogen.

6. The ligand compound according to claim 5, which is represented by Formula 2-1 or Formula 2-2:

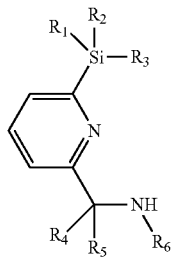

[Formula 2-1]

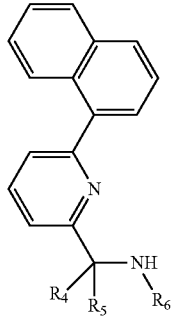

[Formula 2-2]

in Formulae 2-1 and 2-2,

R₁ to R₆ are the same as Formula 2.

7. A catalyst composition, comprising:

the transition metal compound of claim 1; and a cocatalyst.

8. The catalyst composition according to claim 7, wherein the cocatalyst comprises one or more selected from Formulae 4, 5 or 6:

$$-[Al(R_a)-O]_a-$$ [Formula 4]

$$D(R_a)_3$$ [Formula 5]

$$[L-H]^+[Z(A)_4]^-  \text{ or } [L]^+[Z(A)_4]^-$$ [Formula 6]

wherein, each $R_a$ is independently a halogen radical, a hydrocarbyl radical of 1 to 20 carbon atoms, or a halogen-substituted hydrocarbyl radical of 1 to 20 carbon atoms, a is an integer of 2 or more, D is aluminum or boron, L is a neutral or cationic Lewis acid, Z is an element in group 13, each A is independently an aryl group of 6 to 20 carbon atoms or an alkyl group of 1 to 20 carbon atoms, where one or more hydrogen atoms are optionally substituted with a substituent, and the substituent of A is a halogen group, a hydrocarbyl group of 1 to 20 carbon atoms, an alkoxy group of 1 to 20 carbon atoms, or an aryloxy group of 6 to 20 carbon atoms.

9. A method for preparing an olefin polymer, the method comprising:

polymerizing an olefin monomer in the presence of the catalyst composition according to claim 7.

10. The method for preparing an olefin polymer according to claim 9, wherein the olefin monomer is one or more selected from the group consisting of ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene and 1-eicosene.

* * * * *